%

US011078493B2

(12) United States Patent
Makhija et al.

(10) Patent No.: US 11,078,493 B2
(45) Date of Patent: Aug. 3, 2021

(54) SITE-SPECIFIC DNA RECOMBINATION

(71) Applicant: Nanyang Technological University, Singapore (SG)

(72) Inventors: Harshyaa Makhija, Singapore (SG); Peter Droge, Singapore (SG)

(73) Assignee: Nanyang Technological University, Singapore (SG)

(*) Notice: Subject to any disclaimer, the term of this patent is extended or adjusted under 35 U.S.C. 154(b) by 507 days.

(21) Appl. No.: 15/629,334

(22) Filed: Jun. 21, 2017

(65) Prior Publication Data

US 2017/0362606 A1    Dec. 21, 2017

(30) Foreign Application Priority Data

Jun. 21, 2016 (SG) .............................. 10201605079T

(51) Int. Cl.
| | | |
|---|---|---|
| *C12N 15/85* | (2006.01) | |
| *C12N 15/90* | (2006.01) | |
| *C07K 14/705* | (2006.01) | |
| *C07K 16/00* | (2006.01) | |
| *C07K 14/725* | (2006.01) | |
| *C07K 16/28* | (2006.01) | |

(52) U.S. Cl.
CPC .......... *C12N 15/85* (2013.01); *C07K 14/7051* (2013.01); *C07K 14/70578* (2013.01); *C07K 16/00* (2013.01); *C07K 16/2803* (2013.01); *C12N 15/907* (2013.01); *C07K 2317/622* (2013.01); *C07K 2319/00* (2013.01); *C07K 2319/03* (2013.01); *C07K 2319/33* (2013.01); *C12N 2800/107* (2013.01); *C12N 2800/30* (2013.01)

(58) Field of Classification Search
None
See application file for complete search history.

(56) References Cited

FOREIGN PATENT DOCUMENTS

| WO | 01/16345 A2 | 3/2001 | |
|---|---|---|---|
| WO | WO-2009068645 A1 * | 6/2009 | ......... C12N 15/8509 |
| WO | 2016/022075 A1 | 2/2016 | |

OTHER PUBLICATIONS

Christ et al. "Site-specific recombination in eukaryotic cells mediated by mutant λ integrases: implications for synaptic complex formation and the reactivity of episomal DNA segments." Journal of Molecular Biology 319.2 (2002): 305-314. (Year: 2002).*
Chen et al. "Improved production and purification of minicircle DNA vector free of plasmid bacterial sequences and capable of persistent transgene expression in vivo." Human Gene Therapy 16.1 (2005): 126-131. (Year: 2005).*
Altschul et al., "Basic Local Alignment Search Tool," *J. Mol. Biol.*215: 403-410, 1990.
Altschul et al., "Gapped BLAST and PSI-BLAST: a new generation of protein database search programs,"*Nucl. Acids Res.* 25(17): 3389-3402, 1997.
Corona et al., "Activation of site-specific DNA integration in human cells by a single chain integration host factor,"*Nucl. Acids Res.* 31(17): 5140-5148, 2003.
Chandra et al., "Conservative site-specific and single-copy transgenesis in human LINE-1 elements,"*Nucl. Acids Res.*44(6): e55, 2015. (18 pages).
Lorbach et al., "Site-specific Recombination in Human Cells Catalyzed by Phage λ Integrase Mutants," *J. Mol. Biol.* 296: 1175-1181, 2000.
Spengler et al., "The Stereostructure of Knots and Catenanes Produced by Phage λ Integrative Recombination: Implications for Mechanism and DNA Structure," *Cell* 42: 325-334, 1985.

* cited by examiner

*Primary Examiner* — Emily A Cordas
(74) *Attorney, Agent, or Firm* — Seed IP Law Group LLP

(57) ABSTRACT

The present invention provides a method of stably integrating a DNA sequence of interest into a target genomic DNA sequence of a host cell, wherein the target genomic DNA sequence comprises a nucleotide sequence that is at least 80% homologous to the sequence as set forth in SEQ ID NO:1, as well as a kit for use in said method. Also provided is a method of generating a circular DNA construct essentially consisting of a DNA sequence of interest and a nucleotide sequence that is at least 80% homologous to the sequence as set forth in SEQ ID NO:3.

16 Claims, 8 Drawing Sheets

Specification includes a Sequence Listing.

FIG. 5A
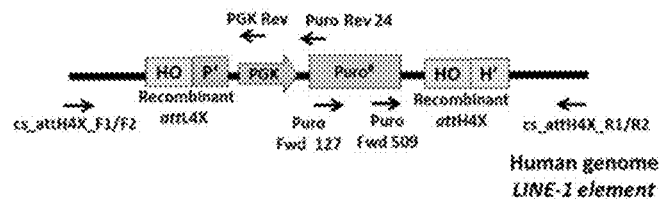
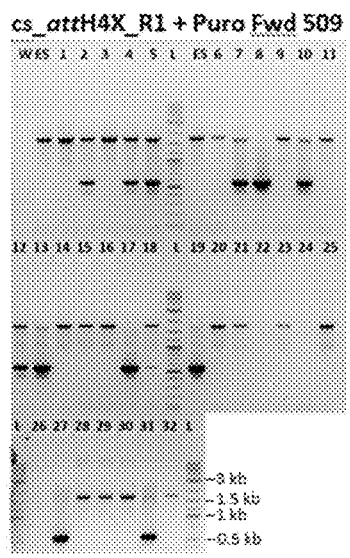
FIG. 5B
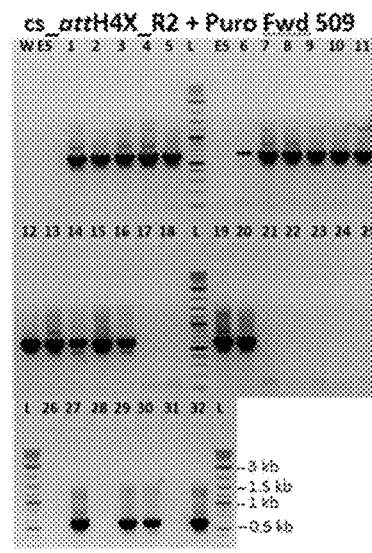
FIG. 5C
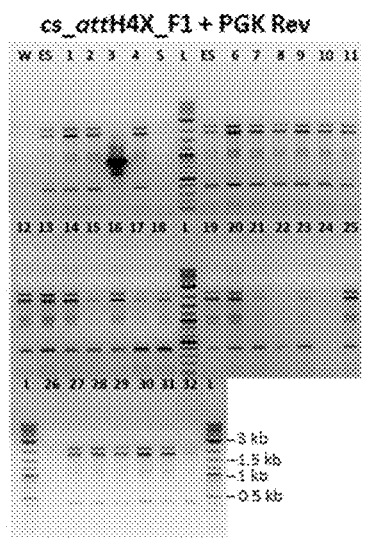
FIG. 5D
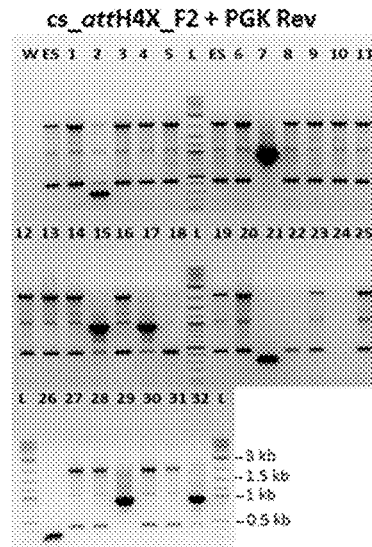
FIG. 5E

SITE-SPECIFIC DNA RECOMBINATION

CROSS-REFERENCE TO RELATED APPLICATION

This application makes reference to and claims the benefit of priority of the Singapore Patent Application No. 10201605079T filed on 21 Jun. 2016, the content of which is incorporated herein by reference for all purposes, including an incorporation of any element or part of the description, claims or drawings not contained herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148 524 SEQUENCE LISTING.txt. The text file is 23.7 KB, was created on Sep. 5, 2017, and is being submitted electronically via EFS-Web.

BACKGROUND

Technical Field

The present invention relates generally to methods of site-specific DNA recombination mediated by phage lambda integrases.

Description of the Related Art

Genome engineering of cells plays an important role in biotechnology and molecular medicine. The recent development of designer endonucleases such as ZFNs, TALENs and CRISPR/Cas9 has also led to more controlled and precise genome engineering. However, there remains a considerable need for alternative technologies for genome engineering.

SUMMARY

The present invention satisfies the aforementioned need in the art by providing novel and versatile methods for site-specific DNA recombination.

In one aspect, the present application relates to a method of stably integrating a DNA sequence of interest into a target genomic DNA sequence of a host cell, wherein the target genomic DNA sequence comprises a nucleotide sequence that is at least 80% homologous to the sequence as set forth in SEQ ID NO:1, the method comprising the steps of:
  (i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising the sequence that is at least 80% homologous to the sequence as set forth in SEQ ID NO:2;
  (ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 and a second circular DNA construct comprising the remainder sequence of the bacterial plasmid and a nucleotide sequence that is at least 80% homologous to the sequence as set forth in SEQ ID NO:4;
  (iii) linearizing the second circular DNA construct by means of an endonuclease activity;
  (iv) isolating the first circular DNA construct comprising the DNA sequence of interest;
  (v) introducing the first circular DNA construct into the host cell, said cell further comprising a phage lambda integrase; and
  (vi) subjecting the host cell to conditions that allow integration of the DNA sequence of interest into the target genomic DNA sequence of the host cell, wherein said integration is mediated by the phage lambda integrase.

In various embodiments, the sequence that is at least 80% homologous to the sequence as set forth in SEQ ID NO:1 and the sequence that is at least 80% homologous to the sequence as set forth in SEQ ID NO:2 flanking the DNA sequence of interest in the bacterial plasmid are arranged in a directly repeated orientation.

In various embodiments, the phage lambda integrase is selected from the group consisting of wild-type Int (SEQ ID NO:5), Int-h (E174K; SEQ ID NO:6), Int-h/218 (E174K/E218K; SEQ ID NO:7), Int-C3 (SEQ ID NO:8), and polypeptide sequences that are at least 80% homologous thereto.

In various embodiments, the phage lambda integrase is N- or C-terminally fused to a nuclear localizing sequence (NLS; SEQ ID NO:9 or a nucleotide sequence that is at least 80% homologous thereto).

In various embodiments, the phage lambda integrase and the first circular DNA construct comprising the DNA sequence of interest are co-introduced or independently introduced into the host cell by DNA transfection, viral transduction, biolistic technology, ultrasound, nanoparticles, or microinjection.

In various embodiments, the intramolecular recombination of step (ii) is carried out in the presence of an IHF variant such as scIHF2 (SEQ ID NO:10).

In various embodiments, the first circular DNA construct comprising the DNA sequence of interest does not contain bacterial sequences, except the nucleotide sequence that is at least 80% homologous to the sequence as set forth in SEQ ID NO:3.

In various embodiments, the DNA sequence of interest comprises one or more genes.

In various embodiments, at least one of the one or more genes is operably linked to expression control sequence(s).

In various embodiments, the DNA sequence of interest comprises a selection marker gene.

In various embodiments, the target genomic DNA sequence comprising the nucleotide sequence as set forth in SEQ ID NO:1 is located in Long Interspersed Elements-1 (LINE-1) elements of the genome of the host cell.

In various embodiments, the host cell is a human cell.

In another aspect, the present application relates to a method of generating a circular DNA construct essentially consisting of a DNA sequence of interest and a nucleotide sequence that is at least 80% homologous to the sequence as set forth in SEQ ID NO:3, the method comprising the steps of:

(i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising a sequence that is at least 80% homologous to the sequence as set forth in SEQ ID NO:2;

(ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 and a second circular DNA construct comprising the remainder sequence of the bacterial plasmid and a nucleotide sequence that is at least 80% homologous to the sequence as set forth in SEQ ID NO:4;

(iii) linearizing the second circular DNA construct by means of an endonuclease activity; and (iv) isolating the first circular DNA construct comprising the DNA sequence of interest.

In various embodiments, the sequence that is at least 80% homologous to the sequence as set forth in SEQ ID NO:1 and the sequence that is at least 80% homologous to the sequence as set forth in SEQ ID NO:2 flanking the DNA sequence of interest in the bacterial plasmid are arranged in a directly repeated orientation.

In various embodiments, the phage lambda integrase is selected from the group consisting of wild-type Int (SEQ ID NO:5), Int-h (E174K; SEQ ID NO:6), Int-h/218 (E174K/E218K; SEQ ID NO:7), Int-C3 (SEQ ID NO:8), and polypeptide sequences that are at least 80% homologous thereto.

In various embodiments, the intramolecular recombination of step (ii) is carried out in the presence of an IHF variant such as scIHF2 (SEQ ID NO:10).

In various embodiments, the first circular DNA construct comprising the DNA sequence of interest does not contain bacterial sequences, except the nucleotide sequence that is at least 80% homologous to the sequence as set forth in SEQ ID NO:3.

In various embodiments, the DNA sequence of interest comprises one or more genes.

In various embodiments, at least one of the one or more genes is operably linked to expression control sequence(s).

In various embodiments, the DNA sequence of interest comprises a selection marker gene.

In still another aspect, the present application relates to a kit for use in the presently disclosed method of stably integrating a DNA sequence of interest into a target genomic DNA sequence of a host cell, wherein the kit comprises any one or more components selected from the group consisting of (a) a bacterial plasmid comprising the DNA sequence of interest of step (i), (b) a phage lambda integrase mediating the intramolecular recombination of step (ii), (c) an endonuclease linearizing the second circular DNA construct of step (iii), (d) a means for isolating the first circular DNA construct of step (iv), (e) a means for introducing the first circular DNA construct into the host cell of step (v), (f) a phage lambda integrase mediating the genomic integration of step (vi) or an expression plasmid encoding the phage lambda integrase, and (g) a means for determining the genomic integration events of step (vi).

In various embodiments, the means for determining the genomic integration events comprises PCR primers.

BRIEF DESCRIPTION OF THE DRAWINGS

The invention will be better understood with reference to the detailed description when considered in conjunction with the non-limiting examples and the accompanying drawings.

FIG. 2A. A schematic diagram showing λ-Int-mediated recombination between genomic attH4X (located in the LINE-1 elements) and attP4X (present in the target vector), leading to site-specific integration of payload into the human LINE-1 elements, then flanked by recombinant sites attL4X (left junction) and attR4X (right junction). FIG. 2B. An illustration depicting in vitro intra-molecular Int-h/218 mediated attH4X×attP4X recombination of a substrate plasmid, resulting in the formation of a seamless vector (after eliminating the undesired bacterial DNA by endonucleolytic digest) comprised of attL4X sequence. The latter can subsequently be targeted at genomic attH4X leading to the insertion of payload through a second λ-Int-mediated recombination event. FIG. 2C. SDS PAGE gel image depicting different desalted fractions of partially purified C-terminally histidine-tagged Int-h/218 (41 kDa). L, Thermo Scientific PAGERULER' prestained protein ladder (10 kDa-250 kDa); E, eluted fraction from desalting column; 1, 2, 3, 4, different desalted fractions of partially purified C-terminal histidine-tagged Int-h/218. FIG. 2D. Representative analysis of an in vitro intra-molecular attH4X ×attP4X recombination with buffers containing different KCl concentrations (in mM) as indicated (left). The two topological DNA forms i.e. supercoiled seamless vector (SC-SV) and open circular seamless vector (OC-SV) obtained after λ-Int mediated recombination were resolved via agarose gel electrophoresis in the presence of ethidium bromide. This resulted in bands for SC-SV and OC-SV, which migrated at ~1.2kb and ~2kb, respectively, whereas the linearized bacterial DNA and the substrate plasmid migrated at ~3kb and ~5.0kb, respectively, as indicated at the left. The purified 1.8 kb seamless vector resulting from in vitro recombination checked by agarose gel electrophoresis is shown at the right: SC-SV and OC-SV.

FIG. 3A. An experimental strategy demonstrating the λ-Int-mediated targeting of seamless vectors for various cell lines. This includes co-transfection of seamless vectors and Int-expressing plasmid, followed by selection, expansion and characterization of the targeted clones using PCR, sequencing and functional studies. FIG. 3B. A schematic illustration showing the targeting of genomic attH4X site with seamless vector attL4X-PGKssPuro by Int-C3, leading to integration of the PGK-Puro cassette. Positions of primers Puro Rev 24, Puro Fwd 127, cs_attH4X_F1/F2 and cs_attH4X_R1/R2 used to identify successful integration at attH4X sites in LINE-1 elements are indicated. FIG. 3C. PCR analysis revealing integration of seamless vector attL4X-PGKssPuro at attH4X site in LINE-1 elements. PCR was performed with primers cs_attH4X_F1/F2 and Puro Rev 24 (left junction) and cs_attH4X_R1/R2 and Puro Fwd 127 (right junction), using genomic DNA from three independent transfections (50 ng, 100 ng and 200 ng) of attL4X-PGKssPuro seamless vector. PCR amplified products of the expected size (~1000 bp; for the left junction) were detected in bulk C3_50, C3_100 and C3_200 (left panels) and (~950 bp; for the right junction) in bulk C3_50, C3_100 and C3_200 (right panels). W, no DNA template control; HT, genomic DNA from HT1080 parental cells. Ina_100/Ina_200: bulk genomic DNA from puromycin resistant clones obtained through co-transfection of 100 ng and 200 ng attL4X-PGKssPuro seamless vector and 1 µg and 2 µg pCMVssIna respectively. C3_50, C3_100, C3_200: bulk genomic DNA from puromycin resistant HT1080 clones obtained through co-transfection of 50 ng, 100 ng and 200 ng of attL4X-PGKssPuro seamless vector with 500 ng, 1 µg, and 2 µg pCMVssInt-C3CNLS, respectively; M1, 1 kb DNA ladder.

FIG. 4A. PCR analysis of attH4X×attL4X recombination events using the genomic DNA from puromycin resistant clones obtained from targeting of seamless vector attL4X-PGKssPuro in HT1080 cells. Position of primers cs_attH4X_R1, cs_attH4X_R2, cs_attH4X_F1, Puro Fwd 127 and Puro Rev 24 to identify recombinant junctions after successful integration at attH4X in LINE-1 elements are indicated. FIG. 4B. PCR screening with cs_attH4X_R1 and Puro Fwd 127 (~950 bp) resulted in 32 positive clones. FIG. 4C. PCR-amplifications with cs_attH4X_R2 and Puro Fwd 127 (~1000 bp) resulted in 33 positive clones. FIG. 4D. PCR with cs attH4X_F1 and Puro Rev 24 (~1100 bp) detected for 13 clones. W, no DNA template control; HT, genomic DNA from HT1080 parental cells; IN, genomic DNA from two puromycin resistant colonies obtained through co-transfection of 50 ng of attL4X-PGKssPuro and 500 ng of pCMVssIna; 1-92, genomic DNA from puromycin resistant clones obtained through co-transfection of 50 ng of attL4X-PGKssPuro and 500 ng of pCMVssInt-C3CNLS; M1, 1 kb DNA ladder.

FIGS. 5A-5E show the screening for attH4X/attL4X recombination events in hES clones. FIG. 5A. PCR screening of attH4X×attL4X recombination events using the genomic DNA from puromycin resistant clones obtained from targeting of seamless vector attL4X-PGKssPuro in hESCs. Recombinant junctions at LINE-1 elements were identified in a screen involving semi-nested PCR with primers cs_attH4X_R1/R2, cs_attH4X_F1/F2, Puro Fwd 509, PGK Rev using the genomic DNA template from primary PCR (with primers Puro Fwd 127 and Puro Rev 24) as indicated. FIG. 5B. PCR amplification with cs_attH4X_R1 and Puro Fwd 509 (~600 bp) resulted in 13 positive clones. FIG. 5C. PCR-amplifications with cs attH4X_R2 and Puro Fwd 509 (~700 bp) were detected for 22 clones. FIG. 5D. PCR screening with cs_attH4X_F1 and PGK Rev (~800 bp) resulted in a single positive clone. FIG. 5E. PCR screening with cs_attH4X_F2 and PGK Rev (~900 bp) resulted in 6 positive clones. W, no DNA template control; ES, genomic DNA from parental hESCs; 1-5, puromycin resistant clones obtained through co-transfection of 100 ng of attL4X-PGKssPuro and 1 µg of pEFssInt-INA; 1-32, puromycin resistant clones obtained through co-transfection of 100 ng of attL4X-PGKssPuro and 1 µg of pEFss-Int-C3CNLS; L, 1 kb DNA ladder.

FIG. 6A. An illustration depicting the PCR strategy for mapping the insertion sites of seamless vector attL4X-PGKssPuro in human HT1080 cells. This includes generation of targeted ssDNA using a biotinylated primer complementary to the inserted vector sequence (step 1), capture of the ssDNA with streptavidin beads, ligation of adenylated oligonucleotide (adaptor) and PCR/sequencing analysis (steps 2-6). Positions of the relevant primers used to map attH4X (right junction) are indicated. FIG. 6B. PCR analysis for mapping insertion sites from HT1080 bulk cell culture. PCR with the primers bpa1 and cs_attH4X_R1 (see step 5), using bulk genomic DNA from co-transfections of 100 ng of attL4X-PGKssPuro and pCMVssInt-C3CNLS resulted in a specific band (highlighted), that was not observed with bulk genomic DNA from control co-transfections of 100 ng of attL4X-PGKssPuro and pCMVssIna. M1, 1 kb ladder; HT, genomic DNA from parental HT1080 cells; INA_100: Bulk genomic DNA from co-transfection of 100 ng of attL4X-PGKsspuro and 1 µg Inactive Int; C3_100: Bulk genomic DNA from co-transfection of 100 ng of attL4X-PGKsspuro and 1 µg Int-C3. W: no DNA template control.

FIG. 7A. A schematic drawing showing in vitro generation and ex vivo targeting of a two-reporter seamless vector (attL4X-PGKssCAR-EF-Puro) at genomic attH4X. Positions of relevant screening primers PGK Rev 187, attP Rev and cs_attH4X_F1/F2 are indicated. The purified 5.5 kb seamless vector resulting from in vitro recombination checked by agarose gel electrophoresis is shown at the left. Supercoiled seamless vector: SC-SV; open circular seamless vector: OC-SV. FIG. 7B. PCR screening of attH4X×attL4X recombination events using the genomic DNA from puromycin resistant clones obtained from targeting of seamless vector attL4X-PGKss-CAR-EF-Puro in hESCs. Recombinant attL4X junction at LINE-1 elements were identified in a screen involving semi-nested PCR with primers cs_attH4X_F1, cs_attH4X_F2, attP Rev using the genomic DNA template from primary PCR (with primers PGK Rev 187) as indicated. PCR with cs_attH4X_F1 and attP Rev (~220 bp) resulted in 10 positive clones (left panel) and PCR screening with cs_attH4X_F2 and attP Rev (~280 bp) resulted in 2 positive clones (right panel). W, no DNA template control; ES, genomic DNA from parental hESCs; I1-I10, puromycin resistant clones obtained through co-transfection of 100 ng of attL4X-PGKssCAR-EF-Puro and 500 ng of pEFssInt-INA; 1-48, puromycin resistant clones obtained through co-transfection of 100 ng of attL4X-PGKssCAR-EF-Puro and 500 ng of pEFssInt-C3CNLS; L, 1 kb DNA ladder. FIG. 7C. Flow cytometric analysis of anti-CD19 CAR expression in targeted hESC clones #19 and 34. A single parameter histogram overlay plots representation of stained non-transfected control hESCs onto the anti-CD19 CAR-stained population resulting from co-transfection of anti-CD19 CAR seamless expression vector with Int-C3 expression plasmid; clone #19 (middle panel) and clone #34 (right panel). An overlay obtained with cells from co-transfection of anti-CD19 CAR seamless expression vector with inactive Int expression plasmid and non-transfected control hESCs after staining is shown in the left panel. The overlay of non-transfected control population onto the transfected population clearly differentiate the anti-CD19 CAR-expressing population seen with Int-C3-transfected clones #19 and 34.

DETAILED DESCRIPTION OF THE INVENTION

Figure 1:
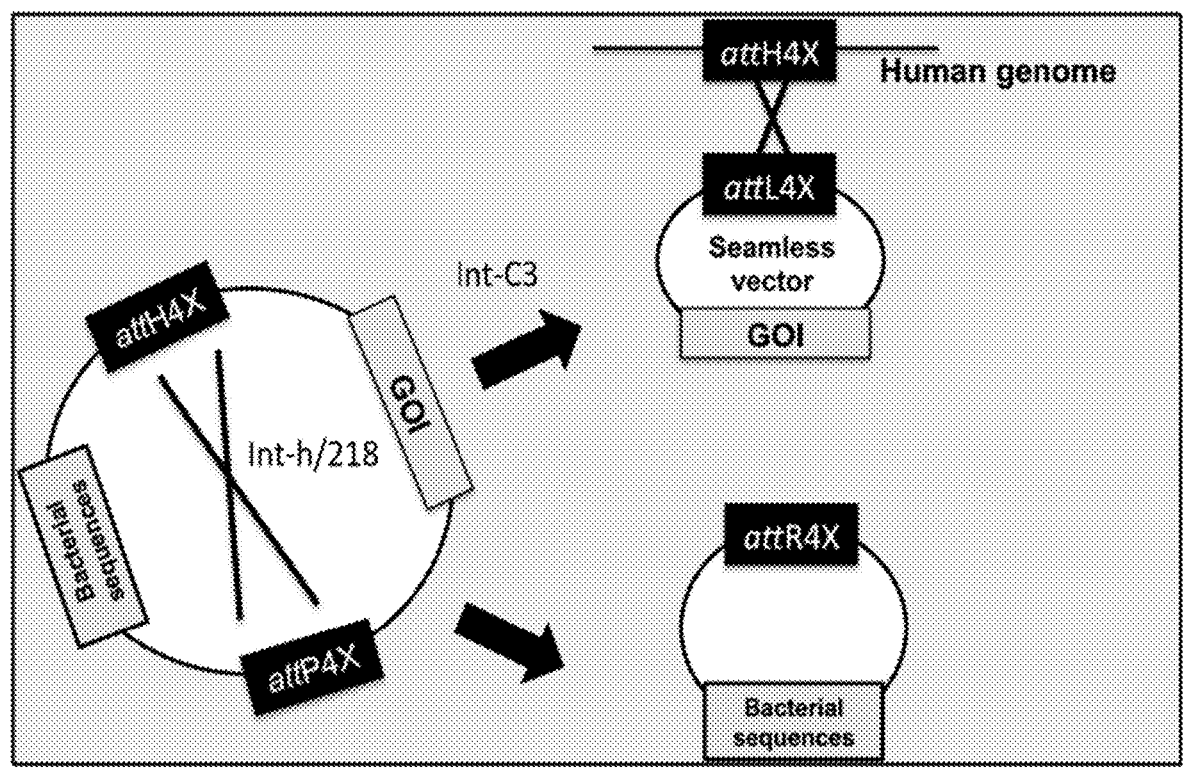
FIG. 1 shows a schematic diagram of the methods of the invention.

The following detailed description refers to, by way of illustration, specific details and embodiments in which the invention may be practiced. These embodiments are described in sufficient detail to enable those skilled in the art to practice the invention. Other embodiments may be utilized and structural and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

The present application provides a novel and versatile platform technology that utilizes a phage lambda integrase for site-specific DNA recombination reactions.

In one aspect, the present application relates to a method of stably integrating a DNA sequence of interest into a target genomic DNA sequence of a host cell, wherein the target genomic DNA sequence comprises a nucleotide sequence that is at least 80% homologous to the sequence as set forth in SEQ ID NO:1, the method comprising the steps of:
  (i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising a sequence that is at least 80% homologous to the sequence as set forth in SEQ ID NO:2;
  (ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 and a second circular DNA construct comprising the remainder sequence of the bacterial plasmid and a nucleotide sequence that is at least 80% homologous to the sequence as set forth in SEQ ID NO:4;
  (iii) linearizing the second circular DNA construct by means of an endonuclease activity;
  (iv) isolating the first circular DNA construct comprising the DNA sequence of interest;
  (v) introducing the first circular DNA construct into the host cell, said cell further comprising a phage lambda integrase; and
  (vi) subjecting the host cell to conditions that allow integration of the DNA sequence of interest into the target genomic DNA sequence of the host cell, wherein said integration is mediated by the phage lambda integrase.

The term "DNA sequence of interest" as used herein refers to any DNA sequence, the manipulation of which may be deemed desirable for any reason (e.g., conferring improved qualities and/or quantities, expression of a protein of interest in a host cell, expression of a ribozyme), by one of ordinary skill in the art. Such DNA sequences include, but are not limited to, coding sequences of structural genes (e.g., reporter genes, selection marker genes, oncogenes, drug resistance genes, growth factor genes), and non-coding sequences which do not encode an mRNA or protein product (e.g., promoter sequences, polyadenylation sequences, termination sequences, enhancer sequences, small interfering RNAs, short hairpin RNAs, antisense RNAs, microRNAs, long non-coding RNAs).

The DNA sequence of interest may comprise one or more genes, which may or may not be operably linked to one or more expression control sequences, such as a promoter, an enhancer, an operator, a termination signal, a 3'-UTR, or a 5'-UTR, an insulator. The term "operably linked" as used herein refers to the relationship between two or more nucleotide sequences that interact physically or functionally. For example, a promoter or regulatory nucleotide sequence is said to be operably linked to a nucleotide sequence that codes for an RNA or a protein if the two sequences are situated such that the regulatory nucleotide sequence will affect the expression level of the coding or structural nucleotide sequence.

The DNA sequence of interest may comprise a selection marker gene. The term "selection marker gene" as used herein refers to a gene that only allows cells carrying the gene to be specifically selected for or against in the presence of a corresponding selection agent. For example, selectable genes commonly used with eukaryotic cells include the genes for aminoglycoside phosphotransferase (APH), hygromycin phosphotransferase (HYG), dihydrofolate reductase (DHFR), thymidine kinase (TK), glutamine synthetase, asparagine synthetase, and genes encoding resistance to neomycin (G418), puromycin, histidinol D, bleomycin and phleomycin.

The term "stably integrating a DNA sequence of interest into a target genomic DNA sequence of a host cell", as used herein, refers to the stable integration of the DNA sequence of interest into the nuclear genome or any other extranuclear genomic material within a cellular compartment of interest, e.g. a mitochondrion, by forming covalent bonds with the host DNA. The stably integrated DNA sequence of interest will thus be heritable to the progeny of a thus modified host cell.

The method of the present invention may be performed in all types of cells in vitro, ex vivo, or in vivo. The host cell may be a eukaryotic cell, preferably a mammalian cell, more preferably a human cell. For example, the host cell may be a bacterial cell, a yeast cell, a plant cell, or a human cell; it may be a cancer cell, an oocyte, an embryonic stem cell, a hematopoietic stem cell, or any type of differentiated cells.

The term "phage lambda integrase" as used herein refers to any phage lambda-derived integrases that possess endonuclease and ligase activities. As known in the art, the phage lambda integrase belongs like Cre and Flp to the integrase family of the sequence-specific conservative DNA recombinases and catalyses the integrative recombination between two different recombination att sites.

The integrase used in the method of the present invention may be the wild-type integrase or any of a variety of homologues or mutants or modified integrases having the integrase activity. Non-limiting examples thereof include all the integrase variants known in the art, e.g. those disclosed in WO2016022075A1 as hereby incorporated by reference.

As the wild-type integrase is only able to perform the recombination reaction with a co-factor, namely IHF, wild-type IHF (composed of IHF alpha and IHF beta subunits set forth in the amino aci sequences of SEQ ID NOs:12 and 13, respectively) or a variant thereof (e.g. scIHF2 as set forth in the amino acid sequence of SEQ ID NO:10) is needed if the wild-type integrase is used. It is therefore preferred to use a modified integrase in the method described herein. The modified integrase is modified such that said integrase may carry out the recombination reaction without IHF.

The generation of modified integrases and the screening for the desired variants are within the knowledge of the skilled person. Preferred integrase variants, especially for step (ii) of the method, are Int-h (E174K; SEQ ID NO:6), Int-h/218 (E174K/E218K; SEQ ID NO:7), and Int-C3 (SEQ ID NO:8), which can function in the presence or absence of IHF (Vijaya et al. Nucleic Acids Res. 2016 Apr. 7; 44(6): e55). Int-C3 is the preferred integrase for carrying out the intermolecular recombination in the host cell. The same or different integrases may be used in steps (ii) and (v) of the method described herein.

The term "bacterial plasmid" as used herein refers to a circular DNA molecule capable of replication in a bacterial host cell. A bacterial plasmid may contain an appropriate origin of replication, which is a sequence of DNA sufficient to enable the replication of the plasmid in a host bacterial cell. A bacterial plasmid may also contain a selectable marker sequence, which encodes a selectable marker conferring cellular resistance to antibiotics such as ampicillin, kanamycin, chloramphenicol, and tetracycline. In preferred embodiments, the bacterial plasmid is negatively (−) supercoiled.

The term "construct" as used herein refers to an artificially assembled DNA segment and can be used interchangeably herein with "plasmid".

In the context of the present application, the nucleotide sequences as set forth in SEQ ID NOs: 1-4 are also referred to as "attH4X", "attP4X", "attL4X", and "attR4X", respectively. An att sequence is the recognition site where binding, cleavage, and strand exchange are performed by the phage lambda integrase and any associated accessory proteins thereof.

The term "at least 80% homologous", "homologue", "variant", or the like as used herein refers to an amino acid or nucleotide sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% of sequence identity with the reference sequence over its entire length. In various embodiments, it has an amino acid or nucleotide sequence that shares at least 80%, preferably at least 85%, more preferably at least 90%, even more preferably at least 95%, and most preferably 100% sequence identity with the reference sequence over its entire length. The identity of nucleic acid sequences or amino acid sequences is generally determined by means of a sequence comparison. This sequence comparison is based on the BLAST algorithm that is established in the existing art and commonly used (cf. e.g. Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

Without wishing to be bound to any particular theory, it is believed that if an integrase-mediated recombination occurs between two compatible recognition sites that are on the same molecule, the intramolecular recombination results in either the deletion or inversion of a sequence flanked by the two recognition sites. More specifically, when two recognition sites on the same DNA molecule are in a directly repeated orientation, integrase excises the DNA between these two sites leaving a single recognition on the DNA molecule; if two recognition sites are in inverted orientation on a single DNA molecule, integrase inverts the DNA sequence between these two sites rather than removing the sequence.

The term "directly repeated orientation" as used herein indicates that the recombination sites in a set of recombinogenic recombination sites are arranged in the same orientation (e.g., 5' to 3'), such that the recombination between these sites results in excision, rather than inversion, of the intervening DNA sequence. The term "inverted orientation" as used herein indicates that the recombination sites in a set of recombinogenic recombination sites are arranged in the opposite orientation, so that the recombination between these sites results in inversion, rather than excision, of the intervening DNA sequence.

Therefore, for the successful implementation of the intramolecular recombination of step (ii) as described herein, the two recognition sites flanking the DNA sequence of interest as described herein are arranged in a directly repeated orientation.

By means of the "intramolecular recombination" between the two lambda integrase recognition sites flanking the DNA sequence of interest, as mediated by a phage lambda integrase, obtained are the first circular DNA construct comprising or essentially consisting of the DNA sequence of interest and the nucleotide sequence that is at least 80% homologous to the sequence as set forth in SEQ ID NO:3 and a second circular DNA construct comprising the remainder sequence of the bacterial plasmid and the nucleotide sequence that is at least 80% homologous to the sequence as set forth in SEQ ID NO:4 (FIG. 1).

The term "essentially consisting of" as used herein is a partially open term, which does not exclude additional, unrecited element(s), step(s), or ingredient(s), as long as these additional element(s), step(s) or ingredient(s) do not materially affect the basic and novel properties of the invention. Said term refers to that the first circular DNA construct consists of the DNA sequence of interest, the nucleotide sequence that is at least 80% homologous to the sequence as set forth in SEQ ID NO:3, and the nucleotide stretches originally present between the DNA sequence of interest and the two flanking sequences defined in step (i). In preferred embodiments, said nucleotide stretches on each side of the DNA sequence of interest have up to 1,000 nt, preferably up to 500 nt, and more preferably up to 100 nt in length. It is preferred that said nucleotide stretches do not make a significant portion (e.g. less than 1%, 5%, or 10%) of the whole construct. In some embodiments, the DNA sequence of interest of the bacterial plasmid are immediately flanked by a sequence that is at least 80% homologous to the sequence as set forth in SEQ ID NO:1and by a sequence that is at least 80% homologous to the sequence as set forth in SEQ ID NO:2, in which case such nucleotide stretches are absent and the resultant first circular DNA construct does not contain bacterial sequences, except the nucleotide sequence that is at least 80% homologous to the sequence as set forth in SEQ ID NO:3. In some embodiments, the bacterial plasmid of the present application is designed with minimized nucleotide stretches insofar as the subsequent intramolecular recombination and the genomic integration of the DNA sequence of interest are not significantly and adversely affected.

Without wishing to be bound to any particular theory, it is believed that intramolecular recombination is thermodynamically strongly favored over intermolecular recombination; hence, under standard reaction conditions, intermolecular recombination is a minor byproduct and even if it occurred, can be clearly distinguished from intramolecular recombination due to molecular size differences. However, the relative concentrations of the bacterial plasmid and the integrase as well as the various parameters of the reaction condition can still be optimized by routine experimentation to favor intramolecular recombination over intermolecular recombination between two different bacterial plasmids.

Consequently, generated is a mini circular plasmid devoid of or essentially devoid of bacterial sequences except the nucleotide sequence that is at least 80% homologous to the sequence as set forth in SEQ ID NO:3.

Such mini circular plasmids provide superior alternatives to traditional plasmids. They exhibit better bioavailability compared to conventional plasmids due to their smaller size, and improved immuno-compatibility due to the reduction or elimination of undesired bacterial sequences. In addition, their smaller size may also confer higher delivery efficiency and lower toxicity.

It should be noted that the first and second circular DNA constructs are generated in the form of catenane rings (Spengler et al., "The stereostructure of knots and catenanes produced by phage lambda integrative recombination: implications for mechanism and DNA structure", Cell, vol. 42, No. 1, August 1985, 325-334). The second circular DNA construct is consequently linearized by means of an endonuclease activity, preferably by means of a restriction enzyme, while leaving the first circular DNA construct intact. The first circular DNA construct is further isolated for use in the following steps. The choice of the endonuclease and the isolation method is within the knowledge of the person of average skill in the art.

The first circular DNA construct comprising the DNA sequence of interest is further introduced into the host cell by any means available in the art, including but not limited to DNA transfection, biolistic technology, ultrasound, nanoparticles, or microinjection. The integrase may be delivered into the host cells either as a polypeptide, mRNA, or via an expression vector, by any means available in the art, including but not limited to DNA transfection, viral transduction, biolistic technology, ultrasound, nanoparticles, microinjection, or HIV Tat-mediated polypeptide delivery. The circular DNA construct and the integrase may be co-introduced or independently introduced into the host cell by the same or different means. In preferred embodiments, the circular DNA construct and a plasmid encoding the integrase are co-transfected into the host cell.

For enhanced recombination efficiency inside the host cell, the integrase used in this step may carry a N- or C-terminal nuclear localization signal (NLS; SEQ ID NO:9 or a nucleotide sequence that is at least 80% homologous thereto).

Without wishing to be bound to any particular theory, it is believed that, if an integrase-mediated recombination occurs between two compatible recombinase recognition sites that are on different molecules (e.g., between a recognition site on a target sequence and a recognition site on a donor sequence), the intermolecular recombination results in the insertion of a sequence from one of the molecules into the other molecule (e.g., the insertion of a donor sequence into a target molecule). In the host cell, the integrase introduced into the host cell is believed to mediate the intermolecular recombination between the nucleotide sequence that is at least 80% homologous to the sequence as set forth in SEQ ID NO:3 of the first circular DNA construct and the nucleotide sequence that is at least 80% homologous to the sequence as set forth in SEQ ID NO:1 of the target genomic DNA, whereby the DNA sequence of interest is inserted into the target genomic DNA sequence in a site-specific manner (FIG. 1).

"Site-specific" means at a particular target DNA sequence, which can be in a specific location in the genome of the host cell. The target DNA sequence can be endogenous to the host cell, either in its natural location in the host genome or at some other location in the genome, or it can be a heterologous nucleotide sequence, which has been previously inserted into the genome of the host cell by any of a variety of known methods. In preferred embodiments, the target genomic DNA sequence comprising the nucleotide sequence as set forth in SEQ ID NO:1 for the stable integration of the DNA sequence of interest is located in Long Interspersed Elements-1 (LINE-1) elements of the genome of the host cell, which occurs approximately 940 times in the human genome.

In another aspect, the present application relates to a method of generating a circular DNA construct essentially consisting of a DNA sequence of interest and a nucleotide sequence that is at least 80% homologous to the sequence as set forth in SEQ ID NO:3, the method comprising the steps of:

(i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising a sequence that is at least 80% homologous to the sequence as set forth in SEQ ID NO:2;

(ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 and a second circular DNA construct comprising the remainder sequence of the bacterial plasmid and a nucleotide sequence that is at least 80% homologous to the sequence as set forth in SEQ ID NO:4;

(iii) linearizing the second circular DNA construct by means of an endonuclease activity; and (iv) isolating the first circular DNA construct comprising the DNA sequence of interest.

As described above, the sequence that is at least 80% homologous to the sequence as set forth in SEQ ID NO:1 thereof and the sequence that is at least 80% homologous to the sequence as set forth in SEQ ID NO:2 flanking the DNA sequence of interest are preferably arranged in a directly repeated orientation.

The phage lambda integrase may be selected from the group consisting of wild-type Int (SEQ ID NO:5), Int-h (E174K; SEQ ID NO:6), Int-h/218 (E174K/E218K; SEQ ID NO:7), Int-C3 (SEQ ID NO:8), and polypeptide sequences that are at least 80% homologous thereto.

The intramolecular recombination of step (ii) may be carried out in the presence of an IHF variant such as scIHF2 (SEQ ID NO:10), especially when wild-type integrase is used.

The resultant first circular DNA construct comprising the DNA sequence of interest may not contain bacterial sequences, except the nucleotide sequence that is at least 80% homologous to the sequence as set forth in SEQ ID NO:3.

The DNA sequence of interest may comprise one or more genes, which may be operably linked to expression control sequence(s). The DNA sequence of interest may comprise a selection marker gene.

In still another aspect, the present application relates to a kit for use in the presently disclosed method of stably integrating a DNA sequence of interest into a target genomic DNA sequence of a host cell, wherein the kit comprises any one or more components selected from the group consisting of (a) a bacterial plasmid comprising the DNA sequence of interest of step (i), (b) a phage lambda integrase mediating the intramolecular recombination of step (ii), (c) an endonuclease linearizing the second circular DNA construct of step (iii), (d) a means for isolating the first circular DNA construct of step (iv), (e) a means for introducing the first circular DNA construct into the host cell of step (v), (f) a phage lambda integrase mediating the genomic integration of step (vi) or an expression plasmid encoding the phage lambda integrase, and (g) a means for determining the genomic integration events of step (vi), e.g. PCR primers for determining said genomic integration events.

The present invention is further illustrated by the following examples. However, it should be understood, that the invention is not limited to the exemplified embodiments.

EXAMPLES

Materials and Methods

Plasmids

Plasmids pattP4X-PGKssPuro-attH4X, pattP4X-PGKss-CAR-EF-Puro-attH4X, pCMVssIna, pCMVssInt-C3CNLS, pEFssInt-C3CNLS, pEFssInt-INA were used.

Cell Lines

Human embryonic stem cell (hESC) line "Genea 047" (Genea Biocells, Sydney, Australia), HT1080 (fibrosarcoma) were used.

Cell Culture

HT1080 was cultured in Dulbecco's Modified Eagle Medium (DMEM) growth medium supplemented with 10% FBS, 1% L-glutamine and 100 Units/ml of Penicillin and Streptomycin each (Gibco, Life technologies) at 37° C. under 5% $CO_2$ in humidified condition. For selection of puromycin-resistant recombinants, puromycin (Gibco, Life technologies) was added in the growth medium (1 µg/ml). Trypsin-EDTA (Gibco, Life technologies) was used for detaching the adherent cells for passaging.

Human Embryonic Stem Cells (GENEA 047) were cultured at 37° C. under 5% $CO_2$ and 5% $O_2$ on Collagen I coated cell culture dishes (Biocoat, Corning) in Genea M2 Medium, (Genea Biocells, Sydney, Australia), supplemented with Penicillin and Streptomycin at 25 Units/ml each (Gibco, Life technologies). For selection of recombinants and maintenance of targeted clones, Puromycin (300 ng/ml) (Gibco, Life technologies) was included in the growth medium. For passaging or preparing cell suspension for reverse transfections, adherent hESCs were rinsed with 1×PBS, detached by incubating at 37° C. for 3 min with passaging solution (Genea Biocells) (with a volume of 100 µl per well of a 6 well plate or 1 ml per 10 cm dish), dislodging cells by tapping and re-suspending the cells with at least 3× volume of Neutralization solution (Genea Biocells). After counting the cells in a haemocytometer (Neubauer), they were pelleted by centrifuging at 300×g for 4 min and resuspended in Genea M2 Medium to the required cell density and added drop-wise to Collagen I-coated dishes.

Transfections

For transfections in HT1080, 3×105 or 3×106 cells were seeded per well of 6 well plate (IWAKI, Japan) or per 10 cm tissue culture dishes (TPP, Switzerland), respectively, in DMEM growth medium a day before transfection to obtain 70-90% confluence at the time of transfection. Transfections were carried out by employing LIPOFECTAMINE® 2000 (Invitrogen, Life technologies) with DNA to LIPOFECTAMINE® 2000 ratio of 1 µg:3 µl. For every transfection per well, DNA and LIPOFECTAMINE® 2000 were incubated separately in 100 µl of OPTI-MEM® medium (Life Technologies). The complexes were then prepared by mixing DNA and LIPOFECTAMINE® 2000 reagent and incubating for 20 min at room temperature. The transfection mix was added drop wise onto the cells (under DMEM growth medium without antibiotics) and transfection was allowed to proceed for 4-6 hours before complexes were removed by fresh DMEM medium.

For transfections in hESCs, FUGENE® HD Transfection reagent (Promega) was used in a reverse transfection protocol. DNA to FUGENE® ratio of 1 µg:3 µl was used. Transfection mixes was prepared by first diluting DNA in 100 µl of OPTI-MEM® and 5 min later the FUGENE® reagent was added to the DNA dilution, mixed and incubated for 15 min at room temperature for the complexes to form. During the incubation period, hESCs were harvested (as described above) and resuspended in Genea M2 Medium (without antibiotics). The transfection complexes were added drop-wise to Collagen 1-coated plates and incubated at culturing conditions for 5 min after which the harvested cells were gently pipetted to the dishes at $5 \times 10^5$ cells per well of 6 well plate and $5 \times 10^6$ cells per 10 cm dish. Transfections were kept overnight under standard culture conditions for hESCs, and media containing transfection complex was replaced with fresh M2 media.

Antibiotic Selection and Screening for Targeted Cell Clones 48h post-transfection, selection with the respective antibiotic in growth medium at the concentrations indicated above was initiated. Selection medium was replaced once in two days until colonies expanded to about 0.3-0.4 cm in diameter. At this stage, the colonies were picked by carefully scraping patches of cells with a pipette tip and transferred to 96 well plates for clonal expansion. The clones were sequentially expanded from 96 wells to 24 wells and subsequently in 6 well plates. Genomic DNA was extracted using DNEASY® Blood & Tissue Kit (Qiagen, GmbH) as per manufacturer's protocol.

Identification of Recombination Events by PCR Screening

PCR was performed using GOTAQ® Flexi DNA polymerase (Promega) to amplify both the junctions using primers listed in the figure descriptions and 500ng of genomic DNA from each recombinant clone or parental cells as template in 50 µl reactions. The thermal cycling parameters used for PCRs was as follows: initial denaturation at 95° C. for 5 min, 35 cycles of denaturation at 95° C. for 1 minute, annealing at 56° C. for 30 seconds and extension at 72° C. for 1 minute, and a final step of 72° C. for 5 min. The PCR samples were analyzed by electrophoresis in 1% agarose (Seakem Agarose, Lonza, USA) gels in 1xTBE (Tris-Boric acid-EDTA buffer) containing 0.5 µg/ml ethidium bromide and PCR-amplified products were compared with DNA standard markers and digitally documented under UV illumination (Quantum Vilber Lourmat, Germany). PCR-amplified products were analyzed by sequencing.

Flow Cytometry

BD LSRFortessa™ X-20 (Becton Dickson, USA) was used to analyze and quantify CAR$^+$ cells. hESCs cells were harvested, centrifuged and suspended in M2 media. Dot plot of side scatter (SSC) versus forward scatter (FSC) was used to gate live cells in order to separate them from aggregated and dead cells. For gated cells, a histogram plot of APC (anti-CD19 CAR$^+$ cells) was constructed. The data was analyzed using FlowJo software and represented as an overlay histogram of stained non-transfected control population onto the stained transfected population that clearly showed the percentage of anti-CD19 CAR expressing population.

Purification of Int-h/218

Plasmid pEFssInt-C3CNLS-H was transformed in *Escherichia coli* (*E. coli*) Rosetta (DE3) pLysS cells and positive clones were screened using LB antibiotics (250 µg/ml ampicillin and 34 µg/ml chloramphenicol) plates. Overnight culture of Rosetta (DE3) pLysS cells overexpressing Int-h/218 was sub-cultured in 200 ml of LB containing ampicillin (250 µg/ml) and chloramphenicol (34 µg/ml) and incubated at 37° C. until the optical density of 0.6 at 650 nm is achieved. At this point, the culture was induced with 0.5 mM IPTG for Int-h/218 overexpression and the induced culture was grown for 6 hours at 30° C. The cell pellet was collected and sonicated in Lysis Buffer (50 mM Tris pH8.0, 2 mM EDTA pH 8.0, 1M KCl, 3 mM PMSF, 5 mM DTT, 10 mM β-mercarptoethanol, 1× protease inhibitor). After removing the cell debris, the cell extract was mixed with Ni-NTA slurry at 4° C. overnight. The Ni-NTA slurry was loaded on the column and the cell extract was collected as a flow through. The slurry was then washed twice with Wash Buffer (50 mM Tris pH8.0, 2 mM EDTA pH 8.0, 1M KCl, 3 mM PMSF, 5 mM DTT, 10 mM β-mercarptoethanol, 20 mM Imidazole, 1× protease inhibitor). The protein was first eluted in Elution Buffer 1 (50 mM Tris pH8.0, 2 mM EDTA pH 8.0, 1M KCl, 3 mM PMSF, 5 mM DTT, 10 mM β-mercarptoethanol, 50 mM Imidazole, 1× protease inhibitor) followed by elution in Elution Buffer 2 (50 mM Tris pH 8.0, 2 mM EDTA pH 8.0, 1M KCl, 3 mM PMSF, 5 mM DTT, 10 mM β-mercarptoethanol, 100 mM Imidazole, 1× protease inhibitor). The eluted fractions were checked for protein in SDS-PAGE gel and the appropriate fractions were desalted using desalting prepacked gravity flow columns (BioRad) in Desalting Buffer (50 mM Tris pH8.0, 2 mM EDTA pH 8.0, 1M KCl, 3 mM PMSF, 5 mM DTT, 10 mM β-mercarptoethanol, 10% Glycerol, 1× protease inhibitor). The desalted fractions were again checked for protein in SDS-PAGE gel and the appropriate fractions were checked for the activity via in vitro recombination reaction.

In Vitro Recombination Using Int-h/218

The in vitro recombination was carried out in a reaction mixture comprised of TE buffer, 600ng of supercoiled substrate plasmid, 0.017 µg/µl of purified single chain IHF, 200 mM KCl and 0.015 µg/µl of partially purified Int-h/218. The reaction mixture was incubated at 37° C. for 2 hours, and DNA was purified using PCR Purification kit (Qiagen, GmbH). The in vitro recombination leads to formation of two catenane rings. One ring is digested with the appropriate restriction enzyme(s) that will only cleave in the bacterial backbone and leaves the supercoiled seamless vector intact. The entire reaction mixture was separated on 1% agarose gel containing 1 µg/ml ethidium bromide at 40V overnight. The seamless vector being covalently closed migrates ahead of the linearized bacterial part of plasmid. The seamless vectors were purified from agarose gels using the QIAQUICK® Gel Extraction Kit (Qiagen, GmbH).

Insertion Mapping

Figure 3A:
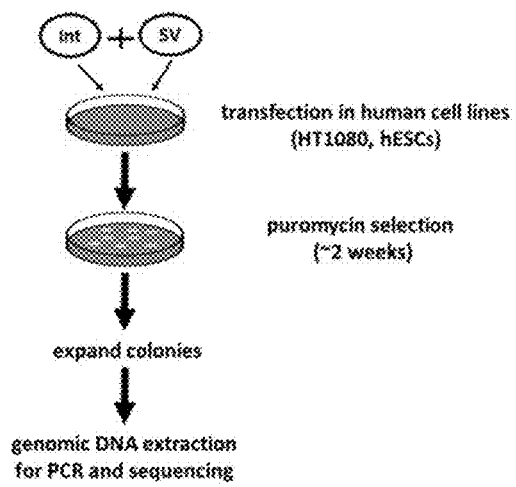
FIGS. 3A-3C show the targeting of seamless vector to LINE-1 elements in HT1080 cells.

The first step of insertion mapping involves using a single biotinylated primer that binds in the known sequence of the inserted vector. The primer will extend, amplify and generate many molecules of the biotinylated ssDNA including the vector sequence and its point of integration into the genome. This ssDNA PCR was performed on genomic DNA from parental HT1080 cells, bulk cultures obtained from co-transfections of seamless vector attL4X-PGKssPuro with pCMVssIna and bulk cultures obtained from co-transfections of seamless vector attL4X-PGKssPuro with pCMVss-Int-C3CNLS. Biotinylated primer Puro Fwd 127 was used to generate the ssDNA extending from puro cassette to the junction of insertion of vector into the human genome (FIG. 3A). PCR was performed using Bioline Taq polymerase with Tris-based buffer (Vivantis) and the reaction conditions includes 95° C., 120 seconds; 95° C., 5 seconds; 50° C., 30 seconds, 72° C., 120 seconds; 50 cycles.

The second step includes capture of ssDNA onto streptavidin dynabeads (M-280 Streptavidin, Thermo Fisher Scientific), which includes washing of dynabeads with 1× PCR buffer (Tris-based) followed by incubation of PCR product generated in the first step with dynabeads for 3 hours on a roller at room temperature. A phosphorylated primer (pETF2-PH) was used as an adaptor and for 5'-adenylation (NEB E2610S). The ligation of the 5' adenylated oligo with captured ssDNA was catalyzed by 5' AppDNA ligase (NEB) at 65° C. for an hour. Semi-nested PCR was performed on beads with forward primer Puro Fwd 128 and reverse primer petF2RC (FIG. 3A) using Taq Polymerase (Bioline) and non-Tris based buffer (Bioline). PCR reaction conditions were 95° C., 120 seconds; 95° C., 5 seconds; 55° C., 30 seconds, 72° C., 120 seconds; 34 cycles. Further, nested PCR was carried with forward primer bpa1 and cs_attH4X_R1 (FIG. 3A), and PCR products were analyzed on 1% agarose gels in 0.5× TBE buffer.

Detection of CAR Expression

Human ESCs were stained with biotin-conjugated AffiniPure F(ab')2 Fragment Goat-anti-Mouse IgG (Jackson Immunoresearch, West Grove, Pa., USA) that reacted with the scFv portion of anti-CD19, followed by streptavidin conjugated to Allophycocyanin (APC; Jackson Immunoresearch, West Grove, Pa., USA).

For detection of anti-CD19 CAR expression on hESCs, 0.25×10$^6$ cells were harvested and washed twice with PBSA (0.1% BSA; 0.1% sodium azide in 1× PBS). This was followed by blocking with 4l of Normal Rabbit Serum (Thermo Fischer Scientific) and staining with biotin-conjugated AffiniPure F(ab')2 Fragment Goat-anti-Mouse IgG at room temperature for 10 mins in the dark. Cells were washed with PBSA twice and incubated with APC-Streptavidin at room temperature for 10 mins in the dark. After washing cells twice with PBSA, the cells were fixed with 300 µl of 0.5% formaldehyde. APC-stained hESCs were detected with BD LSRFortessa™ X-20 (Becton Dickson, USA).

TABLE 1 list of SEQ ID NOs: 1-13

| SEQ ID NO: 1 | attH4X | CTTTATTTCATTAAGTTG |
|---|---|---|
| SEQ ID NO: 2 | attP4X | TCTGTTACAGGTCACTAATACCATCTAAGTAGTTGATTC<br>ATAGTGACTGCATATGTTGTGTTTTACAGTATTATGTAG<br>TCTGTTTTTTATGCAAAATCTAATTTAATATATTGATATT<br>TATATCATTTTACGTTTCTCGTTCAGCTTTATTTCATTAA<br>GTTGGCATTATAAAAAAGCATTGCTTATCAATTTGTTGC<br>AACGAACAGGTCACTATCAGTCAAAATACAATCATTAT<br>TTGATTTC |
| SEQ ID NO: 3 | attL4X | CTGCTTTATTTCATTAAGTTGGCATTATAAAAAAGCATT<br>GCTTATCAATTTGTTGCAACGAACAGGTCACTATCAGTC<br>AAAATACAATCATTATTTGATTTC |
| SEQ ID NO: 4 | attR4X | TCTGTTACAGGTCACTAATACCATCTAAGTAGTTGATTC<br>ATAGTGACTGCATATGTTGTGTTTTACAGTATTATGTAG<br>TCTGTTTTTTATGCAAAATCTAATTTAATATATTGATATT<br>TATATCATTTTACGTTTCTCGTTCAGCTTTATTTCATTAA<br>GTTG |
| SEQ ID NO: 5 | Wildtype Int | M G R R R S H E R R D L P P N L Y I R N N G Y Y C Y R D P<br>R T G K E F G L G R D R R I A I T E A I Q A N I E L F S G H<br>K H K P L T A R I N S D N S V T L H S W L D R Y E K I L A<br>S R G I K Q K T L I N Y M S K I K A I R R G L P D A P L E D<br>I T T K E I A A M L N G Y I D E G K A A S A K L I R S T L S<br>D A F R E A I A E G H I T T N H V A A T R A A K S E V R R<br>S R L T A D E Y L K I Y Q A A E S S P C W L R L A M E L A<br>V V T G Q R V G D L C E M K W S D I V D G Y L Y V E Q S<br>K T G V K I A I P T A L H I D A L G I S M K E T L D K C K E<br>I L G G E T I I A S T R R E P L S S G T V S R Y F M R A R K<br>A S G L S F E G D P P T F H E L R S L S A R L Y E K Q I S D<br>K F A Q H L L G H K S D T M A S Q Y R D D R G R E W D K<br>I E I K |
| SEQ ID NO: 6 | Int-h | M G R R R S H E R R D L P P N L Y I R N N G Y Y C Y R D P<br>R T G K E F G L G R D R R I A I T E A I Q A N I E L F S G H<br>K H K P L T A R I N S D N S V T L H S W L D R Y E K I L A<br>S R G I K Q K T L I N Y M S K I K A I R R G L P D A P L E D<br>I T T K E I A A M L N G Y I D E G K A A S A K L I R S T L S<br>D A F R E A I A E G H I T T N H V A A T R A A K S K V R R<br>S R L T A D E Y L K I Y Q A A E S S P C W L R L A M E L A<br>V V T G Q R V G D L C E M K W S D I V D G Y L Y V E Q S<br>K T G V K I A I P T A L H I D A L G I S M K E T L D K C K E<br>I L G G E T I I A S T R R E P L S S G T V S R Y F M R A R K<br>A S G L S F E G D P P T F H E L R S L S A R L Y E K Q I S D<br>K F A Q H L L G H K S D T M A S Q Y R D D R G R E W D K<br>I E I K |
| SEQ ID NO: 7 | Int-h/218 | M G R R R S H E R R D L P P N L Y I R N N G Y Y C Y R D P<br>R T G K E F G L G R D R R I A I T E A I Q A N I E L F S G H<br>K H K P L T A R I N S D N S V T L H S W L D R Y E K I L A<br>S R G I K Q K T L I N Y M S K I K A I R R G L P D A P L E D<br>I T T K E I A A M L N G Y I D E G K A A S A K L I R S T L S<br>D A F R E A I A E G H I T T N H V A A T R A A K S K V R R<br>S R L T A D E Y L K I Y Q A A E S S P C W L R L A M E L A<br>V V T G Q R V G D L C K M K W S D I V D G Y L Y V E Q S<br>K T G V K I A I P T A L H I D A L G I S M K E T L D K C K E<br>I L G G E T I I A S T R R E P L S S G T V S R Y F M R A R K<br>A S G L S F E G D P P T F H E L R S L S A R L Y E K Q I S D<br>K F A Q H L L G H K S D T M A S Q Y R D D R G R E W D K<br>I E I K |
| SEQ ID NO: 8 | Int-C3 | M G R R R S H E R R D L P P N L Y I R N N G Y Y C Y R D P<br>R T G K E F G L G R D R R I A I T E A I Q A N I E L F S G H<br>K H K P L T A R I N S D N S V T L H S W L D R Y E K I L A<br>S R G I K Q K T L I N Y M S K I K A I R R G L P D A P L E D<br>I T T K E I A A M L N G Y I D E G K A A S A K L I R S T L S<br>D A F R E A I A E G H I T T N H V A A T R A A K S K V R R<br>S R L T A D E Y L K I Y Q A A E S S P C W L R L A M E L A<br>V V T G Q R V G D L C K M K W S D I V D G Y L Y V E Q S<br>K T G V K I A I P T A L H I D A L G I S M K E T L D K C K E<br>I L G G E T I I A S T R R E P L S S G T V S R Y F M R A R K<br>A S G L S F E G D P P T F H E L R S L S A R L Y G K Q I S D<br>K F A Q H L L G H K S V T M A S Q Y R D D R G R E W D K<br>I E I K |
| SEQ ID NO: 9 | SV40 NLS | TCCGGAGGCGGCCCTAAGAAGAAGAGAAAGGTA |

TABLE 1 -continued list of SEQ ID NOs: 1-13

| SEQ ID NO: 10 | scIHF | MASTKSELIERLATQQSHIPAKTVEDAVK<br>EMLEHMASTLAQGGSGGLTKAEMSEYLF<br>DKLGLSKRDAKELVELFFEEIRRALENGE<br>QVKLSGFGNFDLRDKNQRPGRNPKTGEDI<br>PITARRVVTFRPGQKLKSRVENAGGGERIE<br>IRGFGSFSLHYRAPRTGRNPKTGDKVELE<br>GKYVPHFKPGKELRDRANIYGGSGHHHHH<br>H |
|---|---|---|
| SEQ ID NO: 11 | Int-INA | MGRRSHERRDLPPNLYIRNNGYYCYRDP<br>RTGKEFGLGRDRRIAITEAIQANIELFSGH<br>KHKPLTARINSDNSVTLHSWLDRYEKILA<br>SRGIKQKTLINYMSKIKAIRRGLPDAPLED<br>ITTKEIAAMLNGYIDEGKAASAKLIRSTLS<br>DAFREAIAEGHITTNHVAATRAAKSKVRR<br>SRLTADEYLKIYQAAESSPCWLRLAMELA<br>VVTGQRVGDLCKMKWSDIVDGYLYVEQS<br>KTGVKIAIPTALHIDALGISMKETLDKCKE<br>ILGGETIIASTRREPLSSGTVSRYFMRARK<br>ASGLSFEGDPPTFHELRSLSARLYEKQISD<br>KFAQHLLGHKSDTMASQARDDGREWDK<br>IEIK |
| SEQ ID NO: 12 | IHF alpha subunit | MALTKAEMSEYLFDKLGLSKRDAKELVEL<br>FFEEIRRALENGEQVKLSGFGNFDLRDKNQ<br>RPGRNPKTGEDIPITARRVVTFRPGQKLKS<br>RVENASPKDE |
| SEQ ID NO: 13 | IHF beta subunit | MTKSELIERLATQQSHIPAKTVEDAVKE<br>MetLEHMASTLAQGERIEIRGFGSFSLHYRA<br>PRTGRNPKTGDKVELEGKYVPHFKPGKEL<br>RDRANIYG |

TABLE 2 list of primers (5'-3')

| SEQ ID NO: 14 | cs_attH4X_F1 | GAGTGTTTTCCAACTTGGTTCCATT |
|---|---|---|
| SEQ ID NO: 15 | cs_attH4X_R1 | AAAACACAGCACGAGAACTTCGTGA |
| SEQ ID NO: 16 | cs_attH4X_F2 | CCTGTCTTGCTAGGTTGGGAAGT |
| SEQ ID NO: 17 | cs_attH4X_R2 | TAGAGGAATTGCTAACTAGAATAACCA |
| SEQ ID NO: 18 | Puro Fwd 127 | GAGCTGCAAGAACTCTTCCTCAC |
| SEQ ID NO: 19 | Biotinylated Puro fwd 127 | Biotin-GAGCTGCAAGAACTCTTCCTCAC |
| SEQ ID NO: 20 | Puro Rev 24 | CACCGTGGGCTTGTACTCGGTC |
| SEQ ID NO: 21 | PETF2-PH | PHOSPO-CATCGGTGATGTCGGCGATAT |
| SEQ ID NO: 22 | Puro Fwd 128 | CAACAGATGGAAGGCCTCCTGG |
| SEQ ID NO: 23 | petF2RC | ATATCGCCGACATCACCGATG |
| SEQ ID NO: 24 | bpa1 | GGACAGCAAGGGGGAGGATTG |
| SEQ ID NO: 25 | Pgk_rev | CAGGTGAATATCAAATCCTCCTCG |
| SEQ ID NO: 26 | Puro fwd 509 | CTACGAGCGGCTCGGCTTCACC |

Example 1

Generation of Seamless Transgene Target Vectors Through In Vitro Recombination

Figure 2A:
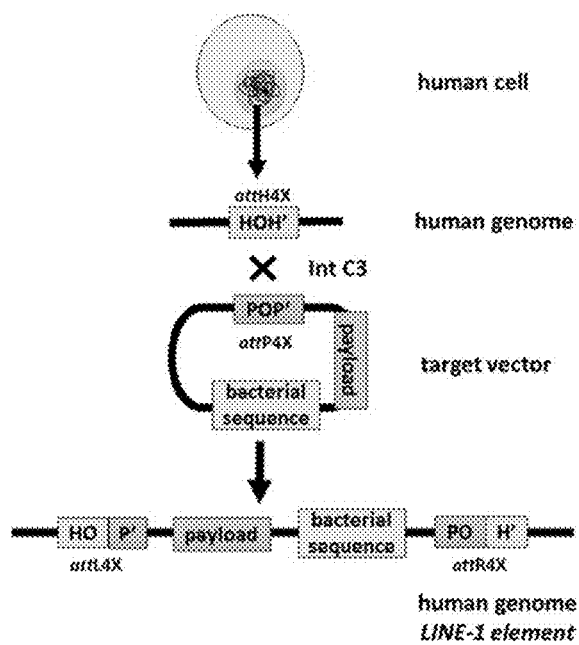
FIGS. 2A-2D show the generation of seamless vectors using λ-Int-mediated genomic recombination.
Figure 2B:
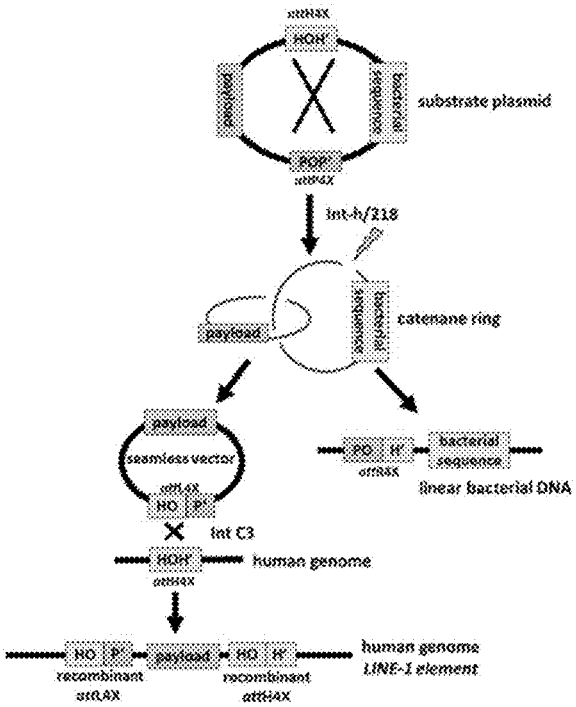

The inventors of the present application demonstrated previously that a 120 bp attL4X hybrid recombination site can functionally replace attP4X for Int-mediated recombination with attH4X in LINE-1. The inventors therefore set out to improve our technology by eliminating the remaining undesired bacterial sequences from target vectors through in vitro attH4X×attP4X intramolecular recombination that results in seamless vectors carrying attL4X, which can be isolated and subsequently recombined with genomic attH4X inside human cells (FIGS. 2A-2B).

Figure 2C:
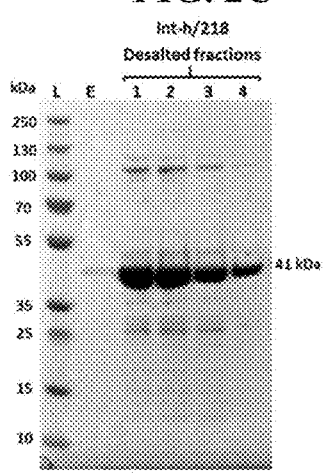
Figure 2D:
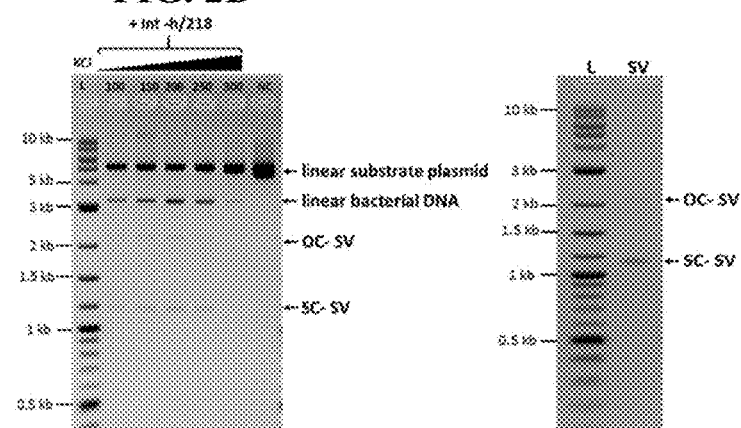

The inventors first established a simple and efficient protocol for partial purification of C-terminally histidine-tagged variant Int-h/218 from *Escherichia coli* (*E. coli*) and produced milligrams of highly enriched active Int-h/218 (FIG. 2C). The partially purified recombinase efficiently catalyzed in vitro intramolecular recombination between directly repeated attP4X and attH4X on a supercoiled plasmid, resulting in a 3.2 kb catenane ring containing unwanted bacterial genetic elements that was subsequently linearized by restriction digest (FIGS. 2B, 2D). The released supercoiled circular seamless target vector (1.8 kb) now carried the payload as well as attL4X as recombination partner for genomic attH4X. Starting, for example, with 10 μg of plasmid DNA, we routinely yielded several μg of mostly supercoiled seamless target vector within 24 hours.

Example 2

Site-Specific Seamless Vector Insertion into Human LINE-1 Elements

The inventors employed the 1.8 kb seamless vector which carried a puromycin expression cassette as a payload plus attL4X to demonstrate site-specific recombination between attL4X and genomic attH4X. Different amounts of seamless DNA were co-transfected into human HT1080 cells with an expression plasmid for either Int-C3 or a recombination-inactive Int variant (Int-INA) (FIG. 3A) The latter harbors an alanine substitution for the scissile bond-forming tyrosine 342. Puromycin selection was applied 48 hours post transfection, and genomic DNA was extracted 2 weeks later and subjected to PCR/sequence analysis (FIGS. 3A-3B).

Figure 3B:
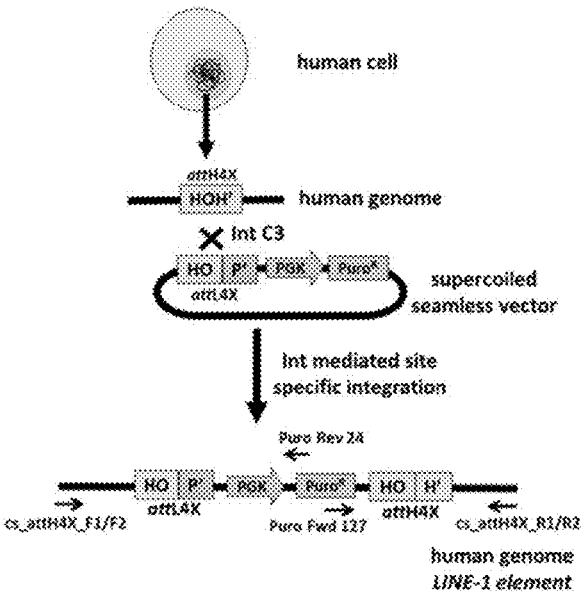
Figure 3C:
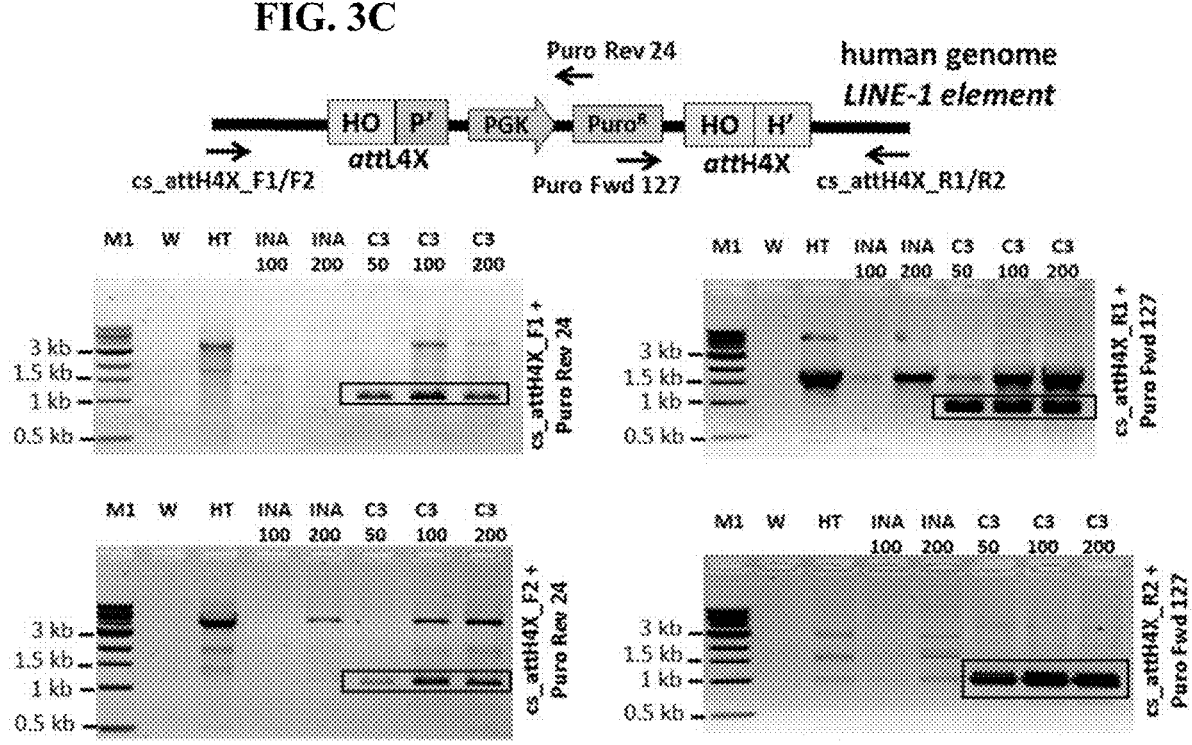
Figure 4A:
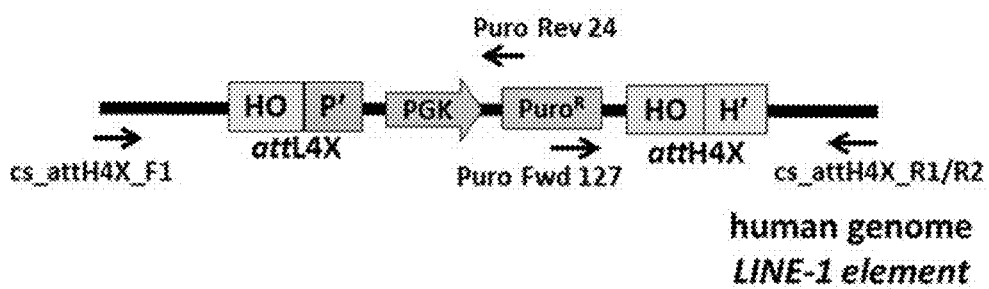
FIGS. 4A-4D show the screening for attH4X/attL4X recombination events in HT1080 clones.
Figure 4B:
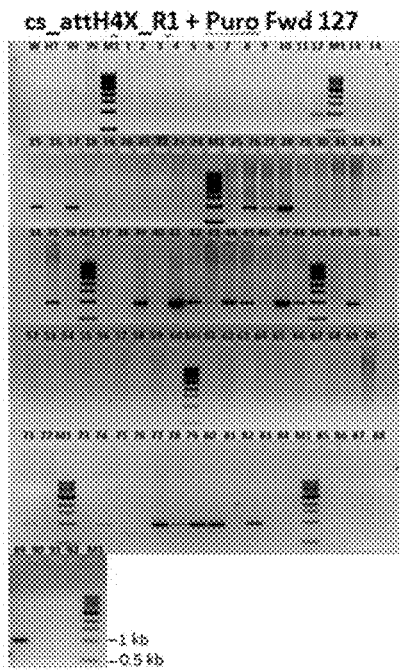
Figure 4C:
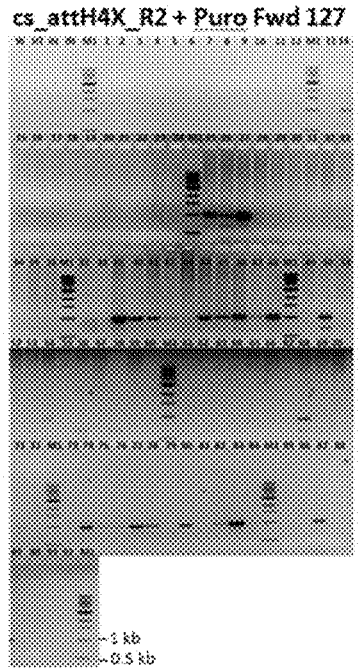
Figure 4D:
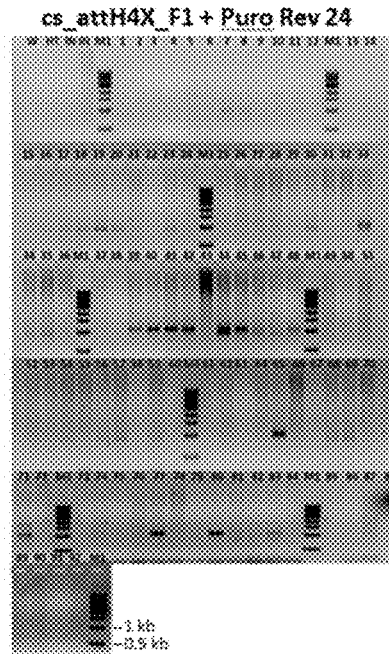

For each amount of transfected seamless vector, bulk cultures were expanded and subsequently screened by genomic PCR using four diagnostic primer pairs employed previously (FIGS. 3B-3C). Expected products were absent from controls and were detectable even with the smallest amount (50 ng) of transfected seamless vector (FIG. 3C). Sequence analysis of these PCR products confirmed targeted seamless vector insertion into LINE-1 (data not shown).

PCR/sequencing was also performed on 92 individual HT1080 colonies that were picked from cells initially transfected with 50 ng of seamless vector. By using three established primer pairs specific for amplification of transgene/genome recombination products, 45 cell clones (~50%) resulting from targeted recombination events were identified, as evidenced by at least one positive PCR signal (FIGS. 4A-4D). Only two colonies were expanded from the control transfection with catalytically inactive Int and no specific PCR products could be detected, indicating that rare illegitimate recombination events led to puromycin resistance (FIGS. 4A-4D). Based on sequence analysis, the inventors were able to identify the loci of the targeted LINE-1 in the 45 clones. In parallel, a similar experiment with hESCs using a seamless vector attL4X-PGKsspuro was performed, where 25/32 clones positive for attH4X targeting in LINE-1 elements were obtained (FIGS. 5A-5E).

Figure 6A:
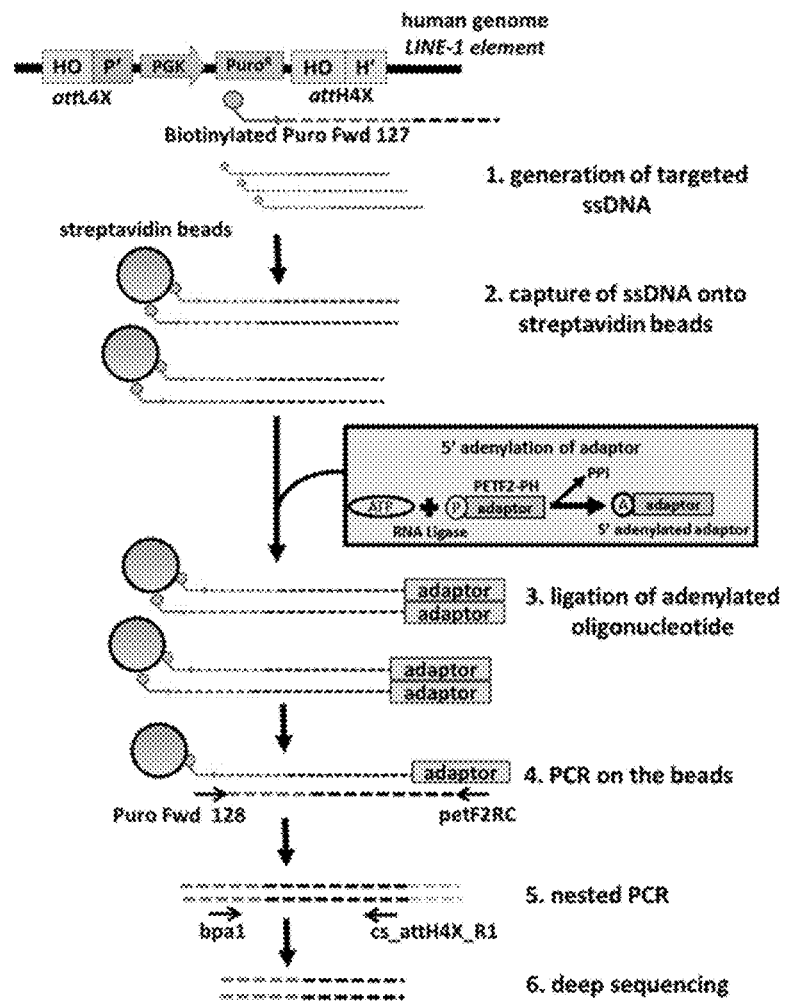
FIGS. 6A-6B show the seamless vector genomic insertion site mapping via deep sequencing.
Figure 6B:
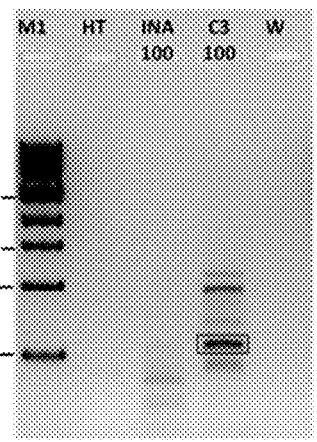

Alongside, a PCR-based strategy was applied to determine targeted LINE-1 loci in a pool of cell clones (FIG. 6A). Using genomic DNA from bulk cultures obtained from transfections of 100 ng of seamless vector, the expected PCR product was only obtained with templates from co-transfections of seamless vector with active Int-C3 (FIG. 6B). Deep paired-end sequencing of these PCR bands resulted in 208,936 reads which contained the expected junction sequence between the vector and attH4X. This corresponded to 26,380 unique sequences which were mapped to the human genome (data not shown)

Example 3

Site-Specific Seamless Vector Transgenesis in Human LINE-1 Elements for Chimeric Antigen Receptor (CAR) Protein Expression In recent years, immunotherapy has emerged as an alternative as well as complementary therapeutic module against cancer. Adoptive T Cell Therapy (ACT) is one of the most compelling immunotherapeutic approaches that have gained significant clinical traction as a therapeutic modality against hematological malignancies, in particular. One of the critical steps of ACT involves genetic engineering of chimeric antigen receptors (CARs) into T cell genome, which is currently being practiced using viral mediated platforms (e.g. retrovirus, lentivirus), and to a lesser extent transposon systems (piggyBac, Sleeping Beauty) for random integration of the CAR gene into the genome of T cells. Despite the clinical success of such engineered T cells, these platforms are qualitatively suboptimal due to the associated inherent limitations such as random insertion of transgenes and the resulting genotoxicity, limitations in cargo size, adverse immune responses and oncogenesis that cannot be overlooked. In addition, advancement in ACT for cancer immunotherapy has also been hindered by the T-cell exhaustion, reinfusions and lack of readily available, functional, antigen-specific enhanced human T lymphocytes which could be overcome by using induced pluripotent stem cells (iPSCs), followed by differentiation into CAR-T-cells.

Figure 7A:
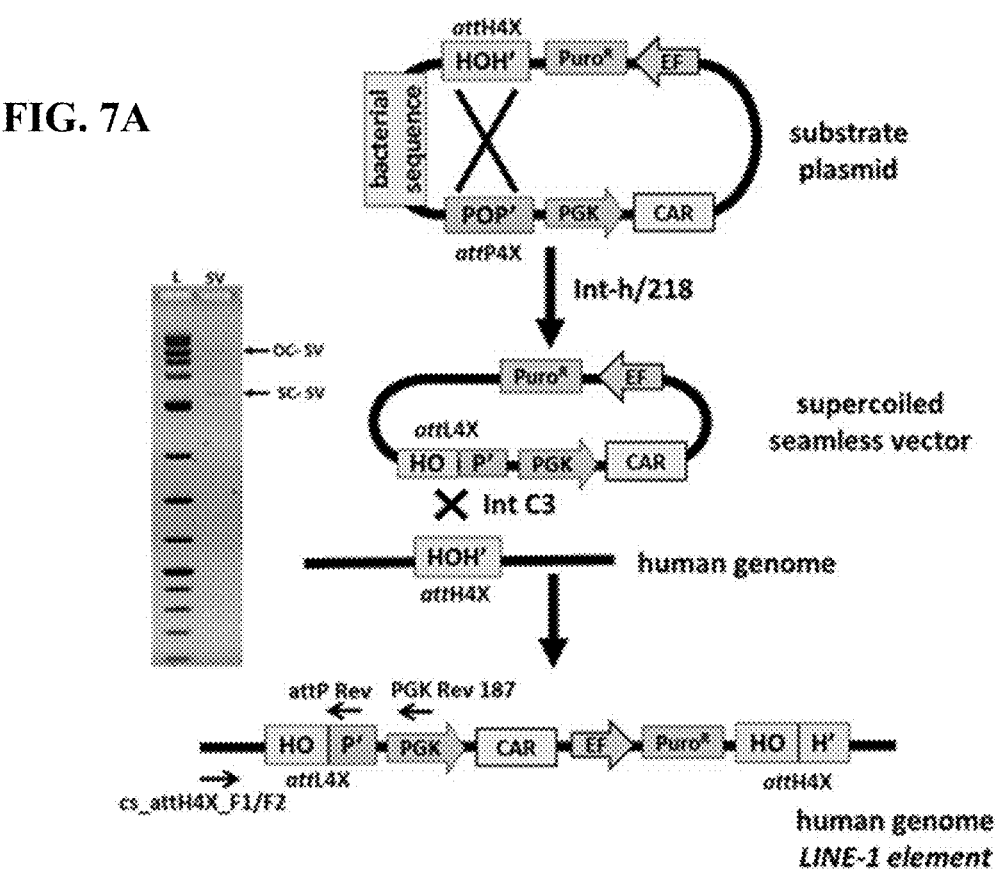
FIGS. 7A-7C show the anti-CD19 CAR expression from seamless vectors in hESCs.
Figure 7B:
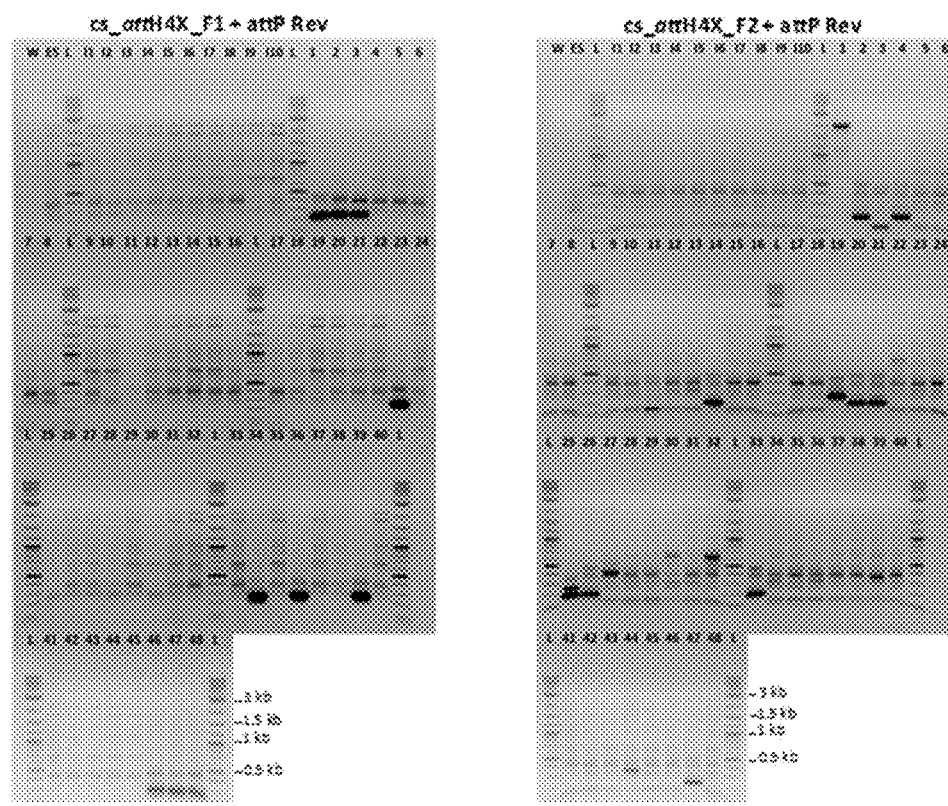
Figure 7C:
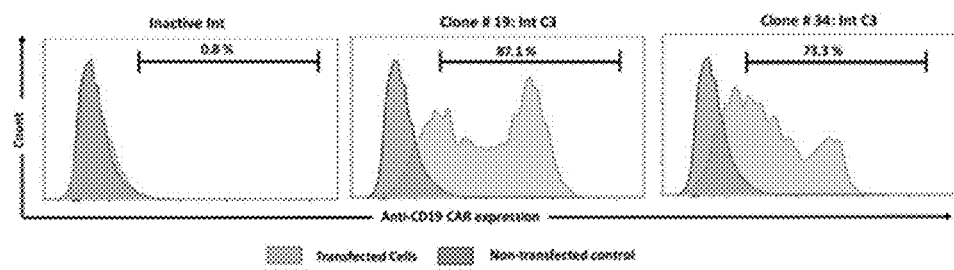

With the aim of targeting an anti-CD19 CAR in hESCs using λ-int technology for immunotherapy of B-cell leukemia and lymphoma, the inventors targeted a multi-reporter attL4X-PGKssCAR-EF-Puro seamless vector construct that expresses an anti-CD19-41BB-CD3zeta CAR into hESCs using the mutant Int C3 as a positive and Int-INA (SEQ ID NO:11) as a negative control (FIG. 7A). The inventors obtained a few puromycin resistant colonies out of which a total of 48 colonies from Int-C3 and 10 colonies from Int-INA transfections were picked for further analysis. The genomic DNA was extracted from all the colonies and a semi-nested PCR was carried out with cs_attH4x_F1/F2 and attP rev primers using a template obtained from primary PCR with cs attH4x_F1/F2 and PGK rev 187 primers. The PCR resulted in 12 clones that were positive for recombinant attL4X junction (FIG. 7B), which were further expanded to test the anti-CD19-CAR expression using FACS. By flow cytometry, 87.1% and 73.3% of cells expressed anti-CD19-CAR in clone #19 and clone #34, respectively, as compared to the Int INA-transfected hESCs (0.8%) (FIG. 7C). The appreciable expression of therapeutic protein CAR in hESCs (FIG. 7C) demonstrates the usefulness of the lambda-integrase technology for therapeutic purposes. In this context, this POC study could serve as a basis for CAR-T based immunotherapy where lambda-integrase mediated recombination system could be used to engineer self-renewable T-cell derived iPSCs with CARs, which can be further differentiated ex vivo to CAR-T-cell lineage.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowl-

What is claimed is:

1. A method of stably integrating a DNA sequence of interest into a target genomic DNA sequence of a host cell, wherein the target genomic DNA sequence comprises a nucleotide sequence that is at least 80% homologous to the sequence as set forth in SEQ ID NO:1, the method comprising the steps of:
   (i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising a nucleotide sequence that is at least 80% homologous to the sequence as set forth in SEQ ID NO:2, wherein the sequence that is at least 80% homologous to the sequence as set forth in SEQ ID NO:1 and the sequence that is at least 80% homologous to the sequence as set forth in SEQ ID NO:2 flanking the DNA sequence of interest are arranged in a directly repeated orientation;
   (ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 that does not contain bacterial sequences, except the nucleotide sequence that is at least 80% homologous to the sequence as set forth in SEQ ID NO:3, and a second circular DNA construct comprising the remainder sequence of the bacterial plasmid and a nucleotide sequence that is at least 80% homologous to the sequence as set forth in SEQ ID NO:4;
   (iii) linearizing the second circular DNA construct by means of an endonuclease activity;
   (iv) isolating the first circular DNA construct comprising the DNA sequence of interest;
   (v) introducing the first circular DNA construct into the host cell, said cell further comprising a phage lambda integrase; and
   (vi) subjecting the host cell to conditions that allow integration of the DNA sequence of interest into the target genomic DNA sequence of the host cell, wherein said integration is mediated by the phage lambda integrase.

2. The method of claim 1, wherein the phage lambda integrase is selected from the group consisting of wild-type Int (SEQ ID NO:5), Int-h (E174K; SEQ ID NO:6), Int-h/218 (E174K/E218K; SEQ ID NO:7) and polypeptide sequences that are at least 80% homologous thereto.

3. The method of claim 2, wherein the phage lambda integrase is N- or C-terminally fused to a nuclear localizing sequence (NLS; SEQ ID NO:9 or a nucleotide sequence that is at least 80% homologous thereto).

4. The method of claim 1, wherein the phage lambda integrase and the first circular DNA construct comprising the DNA sequence of interest are co-introduced or independently introduced into the host cell by DNA transfection, viral transduction, biolistic technology, ultrasound, nanoparticles or microinjection.

5. The method of claim 1, wherein the intramolecular recombination of step (ii) is carried out in the presence of an IHF variant.

6. The method of claim 1, wherein the DNA sequence of interest comprises one or more genes.

7. The method of claim 6, wherein at least one of the one or more genes is operably linked to expression control sequence(s).

8. The method of claim 6, wherein the DNA sequence of interest comprises a selection marker gene.

9. The method of claim 1, wherein the target genomic DNA sequence comprising the nucleotide sequence as set forth in SEQ ID NO:1 is located in Long Interspersed Elements-1 (LINE-1) elements of the genome of the host cell.

10. The method of claim 1, wherein the host cell is a human cell.

11. A method of generating a circular DNA construct essentially consisting of a DNA sequence of interest and a nucleotide sequence that is at least 80% homologous to the sequence as set forth in SEQ ID NO:3, wherein the circular DNA construct comprising the DNA sequence of interest does not contain bacterial sequences, except the nucleotide sequence that is at least 80% homologous to the sequence as set forth in SEQ ID NO:3, and wherein the circular DNA construct comprising the DNA sequence of interest allows integration of the DNA sequence of interest into a target genomic DNA sequence of a host cell by intermolecular recombination mediated by phage lambda integrase, said target genomic sequence comprising a sequence that is at least 80% homologous to the sequence as set forth in SEQ ID NO:1, the method comprising the steps of:
   (i) providing a bacterial plasmid comprising the DNA sequence of interest flanked on a first end by a first nucleotide sequence comprising a sequence that is at least 80% homologous to the sequence as set forth in SEQ ID NO:1 and on a second end by a second nucleotide sequence comprising a sequence that is at least 80% homologous to the sequence as set forth in SEQ ID NO:2, wherein the sequence that is at least 80% homologous to the sequence as set forth in SEQ ID NO:1 and the sequence that is at least 80% homologous to the sequence as set forth in SEQ ID NO:2 flanking the DNA sequence of interest are arranged in a directly repeated orientation;
   (ii) subjecting the bacterial plasmid to conditions that allow intramolecular recombination between the nucleotide sequence that is at least 80% homologous to the sequence as set forth in SEQ ID NO:1 and the nucleotide sequence that is at least 80% homologous to the sequence as set forth in SEQ ID NO:2 in the presence of a phage lambda integrase, to obtain a first circular DNA construct essentially consisting of the DNA sequence of interest and a nucleotide sequence that is at least 80% homologous to the sequence as set forth in SEQ ID NO:3 that does not contain bacterial sequences, except the nucleotide sequence that is at least 80% homologous to the sequence as set forth in SEQ ID NO:3, and a second circular DNA construct comprising the remainder sequence of the bacterial plasmid and the nucleotide sequence that is at least 80% homologous to the sequence as set forth in SEQ ID NO:4;
   (iii) linearizing the second circular DNA construct by means of an endonuclease activity; and
   (iv) isolating the first circular DNA construct comprising the DNA sequence of interest.

12. The method of claim 11, wherein the phage lambda integrase is selected from the group consisting of wild-type Int (SEQ ID NO:5), Int-h (E174K; SEQ ID NO:6), Int-h/218 (E174K/E218K; SEQ ID NO:7), and polypeptide sequences that are at least 80% homologous thereto.

13. The method of claim 11, wherein the intramolecular recombination of step (ii) is carried out in the presence of an IHF variant.

14. The method of claim 11, wherein the DNA sequence of interest comprises one or more genes.

15. The method of claim 14, wherein at least one of the one or more genes is operably linked to expression control sequence(s).

16. The method of claim 14, wherein the DNA sequence of interest comprises a selection marker gene.

* * * * *

SEQUENCE LISTING

```
<160> NUMBER OF SEQ ID NOS: 26

<210> SEQ ID NO 1
<211> LENGTH: 18
<212> TYPE: DNA
<213> ORGANISM: Homo sapiens

<400> SEQUENCE: 1
ctttatttca ttaagttg                                                        18

<210> SEQ ID NO 2
<211> LENGTH: 243
<212> TYPE: DNA
<213> ORGANISM: artificial sequence
<220> FEATURE:
<223> OTHER INFORMATION: a variant of WT attP sequence found in lambda
      phage (Vijaya Chandra, S. H., et al. (2016). "Conservative site-
      specific and single-copy transgenesis in human LINE-1 elements."
      Nucleic Acids Res 44(6): e55.)

<400> SEQUENCE: 2
tctgttacag gtcactaata ccatctaagt agttgattca tagtgactgc atatgttgtg          60
ttttacagta ttatgtagtc tgtttttat gcaaaatcta atttaatata ttgatattta         120
tatcatttta cgtttctcgt tcagctttat ttcattaagt tggcattata aaaaagcatt         180
gcttatcaat ttgttgcaac gaacaggtca ctatcagtca aaatacaatc attatttgat         240
ttc                                                                      243

<210> SEQ ID NO 3
<211> LENGTH: 102
<212> TYPE: DNA
<213> ORGANISM: artificial sequence
<220> FEATURE:
<223> OTHER INFORMATION: a variant of WT attL sequence found in E.Coli
      after recombination (Vijaya Chandra, S. H., et al. (2016).
      "Conservative site-specific and single-copy transgenesis in human
      LINE-1 elements." Nucleic Acids Res 44(6): e55.)

<400> SEQUENCE: 3
ctgctttatt tcattaagtt ggcattataa aaaagcattg cttatcaatt tgttgcaacg          60
aacaggtcac tatcagtcaa aatacaatca ttatttgatt tc                           102

<210> SEQ ID NO 4
<211> LENGTH: 162
<212> TYPE: DNA
<213> ORGANISM: artificial sequence
<220> FEATURE:
<223> OTHER INFORMATION: a variant of WT attR sequence found in E.Coli
      after recombination (Vijaya Chandra, S. H., et al. (2016).
      "Conservative site-specific and single-copy transgenesis in human
      LINE-1 elements." Nucleic Acids Res 44(6): e55.)

<400> SEQUENCE: 4
tctgttacag gtcactaata ccatctaagt agttgattca tagtgactgc atatgttgtg          60
ttttacagta ttatgtagtc tgtttttat gcaaaatcta atttaatata ttgatattta         120
```

```
tatcatttta cgtttctcgt tcagctttat ttcattaagt tg                              162
```

<210> SEQ ID NO 5
<211> LENGTH: 356
<212> TYPE: PRT
<213> ORGANISM: Lambda phage

<400> SEQUENCE: 5

```
Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355
```

```
<210> SEQ ID NO 6
<211> LENGTH: 356
<212> TYPE: PRT
<213> ORGANISM: artificial sequence
<220> FEATURE:
<223> OTHER INFORMATION: Synthetic Int sequence

<400> SEQUENCE: 6

Met Gly Arg Arg Arg Ser His Glu Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355
```

<210> SEQ ID NO 7
<211> LENGTH: 356
<212> TYPE: PRT
<213> ORGANISM: artificial sequence
<220> FEATURE:
<223> OTHER INFORMATION: Sythetic Int sequence

<400> SEQUENCE: 7

```
Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
            355
```

```
<210> SEQ ID NO 8
<211> LENGTH: 356
<212> TYPE: PRT
<213> ORGANISM: artificial sequence
<220> FEATURE:
<223> OTHER INFORMATION: Synthetic Int sequence

<400> SEQUENCE: 8

Met Gly Arg Arg Arg Ser His Glu Arg Asp Leu Pro Pro Asn Leu
1               5                   10                  15

Tyr Ile Arg Asn Asn Gly Tyr Tyr Cys Tyr Arg Asp Pro Arg Thr Gly
                20                  25                  30

Lys Glu Phe Gly Leu Gly Arg Asp Arg Arg Ile Ala Ile Thr Glu Ala
            35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Gly Lys
305                 310                 315                 320

Gln Ile Ser Asp Lys Phe Ala Gln His Leu Leu Gly His Lys Ser Val
                325                 330                 335

Thr Met Ala Ser Gln Tyr Arg Asp Asp Arg Gly Arg Glu Trp Asp Lys
            340                 345                 350

Ile Glu Ile Lys
        355
```

<210> SEQ ID NO 9
<211> LENGTH: 33
<212> TYPE: DNA
<213> ORGANISM: artificial sequence
<220> FEATURE:
<223> OTHER INFORMATION: SV 40 nucleus localizing sequence

<400> SEQUENCE: 9
tccggaggcg gccctaagaa gaagagaaag gta                           33

<210> SEQ ID NO 10
<211> LENGTH: 204
<212> TYPE: PRT
<213> ORGANISM: artificial sequence
<220> FEATURE:
<223> OTHER INFORMATION: Synthetic IHF sequence

<400> SEQUENCE: 10

Met Ala Ser Thr Lys Ser Glu Leu Ile Glu Arg Leu Ala Thr Gln Gln
1               5                   10                  15

Ser His Ile Pro Ala Lys Thr Val Glu Asp Ala Val Lys Glu Met Leu
            20                  25                  30

Glu His Met Ala Ser Thr Leu Ala Gln Gly Gly Ser Gly Gly Leu Thr
        35                  40                  45

Lys Ala Glu Met Ser Glu Tyr Leu Phe Asp Lys Leu Gly Leu Ser Lys
    50                  55                  60

Arg Asp Ala Lys Glu Leu Val Glu Leu Phe Phe Glu Glu Ile Arg Arg
65                  70                  75                  80

Ala Leu Glu Asn Gly Glu Gln Val Lys Leu Ser Gly Phe Gly Asn Phe
                85                  90                  95

Asp Leu Arg Asp Lys Asn Gln Arg Pro Gly Arg Asn Pro Lys Thr Gly
            100                 105                 110

Glu Asp Ile Pro Ile Thr Ala Arg Arg Val Val Thr Phe Arg Pro Gly
        115                 120                 125

Gln Lys Leu Lys Ser Arg Val Glu Asn Ala Gly Gly Gly Glu Arg Ile
    130                 135                 140

Glu Ile Arg Gly Phe Gly Ser Phe Ser Leu His Tyr Arg Ala Pro Arg
145                 150                 155                 160

Thr Gly Arg Asn Pro Lys Thr Gly Asp Lys Val Glu Leu Glu Gly Lys
                165                 170                 175

Tyr Val Pro His Phe Lys Pro Gly Lys Glu Leu Arg Asp Arg Ala Asn
            180                 185                 190

Ile Tyr Gly Gly Ser Gly His His His His His His
        195                 200

<210> SEQ ID NO 11
<211> LENGTH: 356
<212> TYPE: PRT
<213> ORGANISM: artificial sequence
<220> FEATURE:
<223> OTHER INFORMATION: Synthetic Int sequence

<400> SEQUENCE: 11

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
            50                  55                  60

Thr Ala Arg Ile Asn Ser Asp Asn Ser Val Thr Leu His Ser Trp Leu
 65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
            115                 120                 125

Asn Gly Tyr Ile Asp Glu Gly Lys Ala Ser Ala Lys Leu Ile Arg
            130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
            195                 200                 205

Thr Gly Gln Arg Val Gly Asp Leu Cys Lys Met Lys Trp Ser Asp Ile
210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
            275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Ala Arg Asp Asp Arg Gly Arg Glu Trp Asp Lys
            340                 345                 350

Ile Glu Ile Lys
        355

<210> SEQ ID NO 12
<211> LENGTH: 99
<212> TYPE: PRT
<213> ORGANISM: Escherichia coli

<400> SEQUENCE: 12

Met Ala Leu Thr Lys Ala Glu Met Ser Glu Tyr Leu Phe Asp Lys Leu
 1               5                  10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn

```
                    50                  55                  60
Pro Lys Thr Gly Glu Asp Ile Pro Ile Thr Ala Arg Arg Val Val Thr
 65                  70                  75                  80

Phe Arg Pro Gly Gln Lys Leu Lys Ser Arg Val Glu Asn Ala Ser Pro
                 85                  90                  95

Lys Asp Glu

<210> SEQ ID NO 13
<211> LENGTH: 96
<212> TYPE: PRT
<213> ORGANISM: Escherichia coli

<400> SEQUENCE: 13

Met Thr Lys Ser Glu Leu Ile Glu Arg Leu Ala Thr Gln Gln Ser His
  1               5                  10                  15

Ile Pro Ala Lys Thr Val Glu Asp Ala Val Lys Glu Met Glu Thr Leu
                 20                  25                  30

Glu His Met Ala Ser Thr Leu Ala Gln Gly Gly Arg Ile Glu Ile Arg
             35                  40                  45

Gly Phe Gly Ser Phe Ser Leu His Tyr Arg Ala Pro Arg Thr Gly Arg
         50                  55                  60

Asn Pro Lys Thr Gly Asp Lys Val Glu Leu Glu Gly Lys Tyr Val Pro
 65                  70                  75                  80

His Phe Lys Pro Gly Lys Glu Leu Arg Asp Arg Ala Asn Ile Tyr Gly
                 85                  90                  95

<210> SEQ ID NO 14
<211> LENGTH: 25
<212> TYPE: DNA
<213> ORGANISM: artificial sequence
<220> FEATURE:
<223> OTHER INFORMATION: primer

<400> SEQUENCE: 14
gagtgttttc aacttggtt ccatt                                       25

<210> SEQ ID NO 15
<211> LENGTH: 25
<212> TYPE: DNA
<213> ORGANISM: artificial sequence
<220> FEATURE:
<223> OTHER INFORMATION: primer

<400> SEQUENCE: 15
aaaacacagc acgagaactt cgtga                                      25

<210> SEQ ID NO 16
<211> LENGTH: 23
<212> TYPE: DNA
<213> ORGANISM: artificial sequence
<220> FEATURE:
<223> OTHER INFORMATION: primer

<400> SEQUENCE: 16
cctgtcttgc taggttggga agt                                        23

<210> SEQ ID NO 17
<211> LENGTH: 27
<212> TYPE: DNA
<213> ORGANISM: artificial sequence
<220> FEATURE:
<223> OTHER INFORMATION: primer
```

```
<400> SEQUENCE: 17
tagaggaatt gctaactaga ataacca                                              27

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
gagctgcaag aactcttcct cac                                                  23

<210> SEQ ID NO 19
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is biotinylated G.

<400> SEQUENCE: 19
nagctgcaag aactcttcct cac                                                  23

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
caccgtgggc ttgtactcgg tc                                                   22

<210> SEQ ID NO 21
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is phosphorylated C.

<400> SEQUENCE: 21
natcggtgat gtcggcgata t                                                    21

<210> SEQ ID NO 22
<211> LENGTH: 22
<212> TYPE: DNA
<213> ORGANISM: artificial sequence
<220> FEATURE:
<223> OTHER INFORMATION: primer

<400> SEQUENCE: 22
caacagatgg aaggcctcct gg                                                   22

<210> SEQ ID NO 23
<211> LENGTH: 21
<212> TYPE: DNA
<213> ORGANISM: artificial sequence
<220> FEATURE:
```

```
<223> OTHER INFORMATION: primer

<400> SEQUENCE: 23
atatcgccga catcaccgat g                                        21

<210> SEQ ID NO 24
<211> LENGTH: 21
<212> TYPE: DNA
<213> ORGANISM: artificial sequence
<220> FEATURE:
<223> OTHER INFORMATION: primer

<400> SEQUENCE: 24
ggacagcaag ggggaggatt g                                        21

<210> SEQ ID NO 25
<211> LENGTH: 24
<212> TYPE: DNA
<213> ORGANISM: artificial sequence
<220> FEATURE:
<223> OTHER INFORMATION: primer

<400> SEQUENCE: 25
caggtgaata tcaaatcctc ctcg                                     24

<210> SEQ ID NO 26
<211> LENGTH: 22
<212> TYPE: DNA
<213> ORGANISM: artificial sequence
<220> FEATURE:
<223> OTHER INFORMATION: primer

<400> SEQUENCE: 26
ctacgagcgg ctcggcttca cc                                       22
```